United States Patent
Yeatman et al.

(10) Patent No.: US 9,057,108 B2
(45) Date of Patent: Jun. 16, 2015

(54) HYBRID MODEL FOR THE CLASSIFICATION OF CARCINOMA SUBTYPES

(75) Inventors: Timothy Yeatman, Thonotosassa, FL (US); Barbara A. Centeno, Tampa, FL (US); Gregory C. Bloom, Tampa, FL (US)

(73) Assignee: H. Lee Moffitt Cancer and Research Institute, Inc., Tampa, FL (US)

( * ) Notice: Subject to any disclaimer, the term of this patent is extended or adjusted under 35 U.S.C. 154(b) by 101 days.

(21) Appl. No.: 13/611,584

(22) Filed: Sep. 12, 2012

(65) Prior Publication Data

US 2013/0172203 A1    Jul. 4, 2013

Related U.S. Application Data

(63) Continuation of application No. PCT/US2011/029208, filed on Mar. 21, 2011.

(60) Provisional application No. 61/315,726, filed on Mar. 19, 2010.

(51) Int. Cl.
| | |
|---|---|
| *C12Q 1/68* | (2006.01) |
| *G01N 33/574* | (2006.01) |
| *G06F 19/20* | (2011.01) |
| *G06F 19/24* | (2011.01) |

(52) U.S. Cl.
CPC ........ *C12Q 1/6886* (2013.01); *C12Q 2600/112* (2013.01); *C12Q 2600/158* (2013.01); *G01N 33/574* (2013.01); *G06F 19/20* (2013.01); *G06F 19/24* (2013.01); *G01N 33/57484* (2013.01)

(58) Field of Classification Search
None
See application file for complete search history.

(56) References Cited

U.S. PATENT DOCUMENTS

| | | | |
|---|---|---|---|
| 5,514,554 | A | 5/1996 | Bacus |
| 2005/0123945 | A1 | 6/2005 | Torres-Roca et al. |
| 2006/0003359 | A1 | 1/2006 | Feinberg et al. |
| 2006/0211036 | A1 | 9/2006 | Chou et al. |
| 2008/0281568 | A1 | 11/2008 | Kao et al. |

OTHER PUBLICATIONS

Moraweitz et al (2010) "Comparison of histopathological and gene expression-based typing of cancer of unknown primary" Virchows Arch 456:23-29.*
Oien, K.A. (2009) "Pathologic Evaluation of Unknown Primary Cancer" Seminars in Oncology, vol. 36, No. 1, pp. 8-37.*
Bloom, et al., Multi-platform, multi-site, microarray-based human tumor classification, American Journal Pathology, vol. 164, No. 1, Jan. 2004, pp. 9-16.
Bridgewater, et al., Gene expression profiling may improve diagnosis in patients with carcinoma of unknown primary, British Journal of Cancer, vol. 98, 2008, pp. 1425-1430.
Buckhaults, et al., Identifying tumor origin using a gene expression-based classification map, Cancer Research, vol. 63, Jul. 15, 2003, pp. 4144-4149.
Cai, et al. Cytokeratin 7 and 20 and thyroid transcription factor 1 can help distinguish pulmonary from gastrointestinal carcinoid and pancreatic endocrine tumors, Hum Pathology, vol. 32, No. 10, Oct. 2001, pp. 1087-1093.
Chu, et al, Expression of cytokeratin 5/6 in epithelial neoplasms: an immunohistochemical study of 509 cases, Modern Pathology, 2002, vol. 15, No. 1, pp. 6-10.
Dennis, et al., Identification from public data of molecular markers of adenocarcinoma characteristic of the site of origin, Cancer Research, vol. 62, 2002, pp. 5999-6005.
Eisenthal et al., Expression of Dendritic Cells in Ovarian Tumors Correlates with Clinical Outcome in Patients with Ovarian Cancer, Human Pathology, vol. 32, No. 8, Aug. 2001, pp. 803-807.
Eschrich, et al., Tissue-Specific RMA models to incrementally normalize Affymetrix GeneChip Data, 30th Annual International IEEE EMBS Conference, Vancouver, British Columbia, Canada, Aug. 20-24, 2008, pp. 2419-2422.
Giordano, et al., Organ-specific molecular classification of primary lung, colon, and ovarian adenocarcinomas using gene expression profiles, American Journal of Pathology, vol. 159, No. 4, Oct. 2001, pp. 1231-1238.
Jakobsen, et al., Expression of synaptic vesicle protein 2 (SV2) in neuroendocrine tumors of the gastrointestinal tract and pancreas, Journal Pathology 2002, vol. 196, pp. 44-50.
Jakobsen, et al., NESP55, a novel chromogranin-like peptide, is expressed in endocrine tumors of the pancreas and adrenal medulla but not in ileal carcinoids, British Journal of Cancer 2003, vol. 88, pp. 1746-1754.
Kargi, et al., The diagnostic value of TTF-1, CK 5/6, and p63 immunostaining in classification of lung carcinomas, Appl Immunohistochem Mol Morphol 2007, vol. 15, No. 4, pp. 415-420.
Kaufmann, et al., Value of p63 and cytokeratin 5/6 as immunohistochemical markers for the differential diagnosis of poorly differentiated and undifferentiated carcinomas, Am J Clin Pathol 2001, vol. 116 pp. 823-830.
Khayyata, et al., Value of P63 and CK5/6 in distinguishing squamous cell carcinoma from adenocarcinoma in lung fine-needle aspiration specimens, Diagnostic Cytopathology 2009, vol. 37, No. 3, pp. 178-183.

(Continued)

*Primary Examiner* — Tracy Vivlemore
*Assistant Examiner* — Karen S Weiler
(74) *Attorney, Agent, or Firm* — Michele L. Lawson; Smith & Hopen, P.A.

(57) ABSTRACT

A two-tiered classification system that can be integrated with the current algorithm used by pathologists for identification of the site of origin for 'malignancy with unknown primary' is presented. In use, morphology, immunohistochemical (IHC) studies, and microarray-based top tier gene expression classifiers first subclassify cytokeratin positive carcinomas into adenocarcinoma, squamous cell carcinoma, neuroendocrine carcinoma and urothelial carcinoma. Subsequently, organ-specific IHC-markers, if available, are used in conjunction with microarray-based second tier gene expression classifiers to assign the primary site of origin to the sample. This new hybrid approach combines IHC with a hierarchy of quantitative gene expression based classifiers into an algorithmic method that can assist pathologists to further refine and support their decision making process.

21 Claims, 11 Drawing Sheets

(56) References Cited

OTHER PUBLICATIONS

Ma, et al., Molecular classification of human cancers using a 92-gene real-time quantitative polymerase chain reaction assay, Arch Pathol Lab Med 2006, vol. 130, pp. 465-473.

Monica, et al., Desmocollin-3: a new marker of squamous differentiation in undifferentiated large-cell carcinoma of the lung, Modern Pathology 2009, vol. 22, pp. 709-717.

Monzon, et al., Diagnosis of Metastatic Neoplasms: Molecular Approaches for Identification of Tissue of Origin. Arch Pathol Lab Med. 2010. vol. 134, pp. 216-224.

Portela-Gomes, et al., Synaptic vesicle protein 2, A new neuroendocrine cell marker, Am J Pathol 2000, vol. 157, No. 4, pp. 1299-1309.

Ramaswamy, et al., Multiclass cancer diagnosis using tumor gene expression signatures, Proc Nati Acad Sci USA, 2001, vol. 98, No. 26, pp. 15149-15154.

Serrano, et al., Utility of high molecular weight cytokeratins, but not p63, in the differential diagnosis of neuroendocrine and basaloid carcinomas of the head and neck, Human Pathology 2008, vol. 39, pp. 591-598.

Shedden, et al., Accurate molecular classification of human cancers based on gene expression using a simple classifier with a pathological tree-based framework, American Journal of Pathology 2003, vol. 163, No. 5, pp. 1985-1995.

Srivastava, et al., Neuroendocrine secretory protein-55 (NESP-55) expression discriminates pancreatic endocrine tumors and pheochromocytomas from gastrointestinal and pulmonary carcinoids, Am J Surg Pathol 2004, vol. 28, No. 10, pp. 1371-1378.

Srivastava, et al., Immunohistochemical staining for CDX-2, PDX-1, NESP-55, and TTF-1 can help distinguish gastrointestinal carcinoid tumors from pancreatic endocrine and pulmonary carcinoid tumors, Am J Surg Pathol 2009, vol. 33, pp. 626-632.

Su, et al., Molecular Classification of Human Carcinomas by Use of Gene Expression Signatures, Cancer Research 2001, vol. 61, pp. 7388-7393.

Sugai, et al., Expression of hepatocyte nuclear factor 4a in primary ovarian mucinous tumors, Pathology Intrnational 2008, vol. 58, pp. 681-686.

Talbot, et al., Gene expression profiling allows distinction between primary and metastatic squamous cell carcinomas in the lung, Cancer Research 2005, vol. 65, No. 8, pp. 3063-3071.

Tothill, et al., An expression-based site of origin diagnostic method designed for clinical application to cancer of unknown origin, Cancer Research 2005, vol. 65, pp. 4031-4040.

Vachani, et al., A 10-gene classifier for distinguishing head and neck squamous cell carcinoma and lung squamous cell carcinoma, Clinical Cancer Research 2007, vol. 13, pp. 2905-2915.

Yao, et al., One hundred years after "carcinoid": epidemiology of and prognostic factors for neuroendocrine tumors in 35,825 cases in the United States, Journal Clinical Oncology 2008, vol. 26, No. 18, pp. 3063-3072.

International Preliminary Report on Patentability for application No. PCT/US2011/029208, filing date of Mar. 21, 2011.

International Search Report for application No. PCT/US2011/029208, filing date of Mar. 21, 2011.

Talantov D, et al. A quantitative reverse transcriptase-polymerase chain reaction assay to identify metastatic carcinoma tissue of origin. Journal of Molecular Diagnostics, vol. 8, No. 3, Jul. 2006. pp. 320-329.

Varadhachary GR, et al. Molecular profiling of carcinoma of unknown primary and correlation with clinical evaluation. Journal of Clinical Oncology. vol. 26, No. 27, Sep. 20, 2008. pp. 4442-4448.

Monzon FA et al. Multicenter validation of a 1,550-gene expression profile for identification of tumor tissue of origin. Journal of Clinical Oncology. vol. 27, No. 15, May 20, 2009. pp. 2503-2508.

Pillai R. et al. A microarray-based gene expression test for tumors with uncertain origins using formalin-fixed, paraffin-embedded specimens. Pathwork Diagnostics. Abstracts and Case Studies from the College of American Pathologists. Oct. 2009 Annual Meeting. Arch. Pathol. Lab. Med., vol. 133.

Horlings HM, et al. Gene expression profiling to identify the histogenetic origin of metastatic adenocarcinomas of unknown primary. Journal of Clinical Oncology, vol. 26, No. 27, Sep. 20, 2008. pp. 4435-4441.

Rosenfield N, et al. MicroRNAs accurately identify cancer tissue origin. Nature Biotechnology, vol. 26, No. 4, Apr. 2008. pp. 462-469.

Gerdin A.K. et al., Phenotypic screening of hepatocyte nuclear factor (HNF) 4-gamma receptor knockout mice. Biochemical and Biophysical Research Communications, vol. 349, (2006) pp. 825-832.

Barbara A. Centeno, et al., Hybrid Model for the Classification of Carcinoma Subtypes. pp. 1-16, submitted for review Aug. 19, 2009.

\* cited by examiner

IGC Data: Top Primary Sites per Histological Subtype

| Histologic subtype | Primary site | Number |
| --- | --- | --- |
| Adenocarcinoma | Vulva | 1 |
| Adenocarcinoma | Vagina | 1 |
| Adenocarcinoma | Appendix | 1 |
| Adenocarcinoma | Duodenum | 1 |
| Adenocarcinoma | GI tract, NOS | 2 |
| Adenocarcinoma | GE junction | 2 |
| Adenocarcinoma | Gallbladder | 2 |
| Adenocarcinoma | Breast | 3 |
| Adenocarcinoma | Small intestine | 3 |
| Adenocarcinoma | Unknown | 5 |
| Adenocarcinoma | Esophagus | 5 |
| Adenocarcinoma | Fallopian tube | 6 |
| Adenocarcinoma | Stomach | 9 |
| Adenocarcinoma | Cervix | 9 |
| Adenocarcinoma | Peritoneum | 12 |
| Adenocarcinoma | Pancreas | 17 |
| Adenocarcinoma | Colon (rectosigmoid) | 35 |
| Adenocarcinoma | Colon (rectum) | 36 |
| Adenocarcinoma | Lung | 55 |
| Adenocarcinoma | Prostate | 59 |
| Adenocarcinoma | Ovary | 117 |
| Adenocarcinoma | Uterus | 157 |
| Adenocarcinoma | Colon | 254 |
| Neuroendocrine | Small intestine | 1 |
| Neuroendocrine | Pancreas | 2 |
| Neuroendocrine | Lung | 7 |
| Squamous | Parotid | 1 |
| Squamous | Pharynx | 1 |
| Squamous | Penis | 1 |
| Squamous | Kidney | 1 |
| Squamous | Skin | 2 |
| Squamous | Tongue | 2 |
| Squamous | Bladder | 3 |
| Squamous | Vulva | 7 |
| Squamous | Cervix | 24 |
| Squamous | Lung | 37 |
| Urothelial | Ureterovesicle | 1 |
| Urothelial | Urinary tract | 1 |
| Urothelial | Ureter | 3 |
| Urothelial | Kidney | 9 |
| Urothelial | Bladder | 27 |

Figure 4

Histologic Type and Primary Site of Origin for Specimens Obtained from H. Lee Moffitt Cancer Center Tissue Procurement Facility

| Site of origin | Carcinoma type | Total | Subtypes | Grades |
|---|---|---|---|---|
| Stomach | Adenocarcinoma | 39 | 16 signet ring cell | Grade 1:7 |
| | | | 20 intestinal | Grade 2:13 |
| | | | 3 mucinous | Grade 3:19 |
| Bladder, ureters, renal pelvis | Urothelial carcinoma | 25 | No specific subtypes | 24 high-grade |
| | | | | 1 low-grade |
| Liver | Hepatocellular carcinoma | 31 | 1 fibrolamellar | Grade 1:8 |
| | | | 1 clear cell | Grade 2:15 |
| | | | 29 NOS | Grade 3:6 |
| | | | | Grade 4:1 |
| | | | | Grade X:1 |
| Kidney | Renal cell | 61 | 27 clear cell | Clear cell grades |
| | | | 10 sarcomatoid | Grade 1:6 |
| | | | 16 papillary | Grade 2:7 |
| | | | 8 chromophobe | Grade 3:8 |
| | | | | Grade 4:6 |
| Breast | Adenocarcinoma | 73 | 42 ductal | |
| | | | 19 lobular | |
| | | | 12 mixed | |
| Anus, rectum, colon | Squamous cell carcinoma | 12 | | Grade 1:3 |
| | | | | Grade 2:3 |
| | | | | Grade 3:6 |
| Esophagus | Squamous cell carcinoma | 5 | | Grade 1:0 |
| | | | | Grade 2:4 |
| | | | | Grade 3:1 |
| Larynx | Squamous cell carcinoma | 42 | | Grade 1:7 |
| | | | | Grade 2:20 |
| | | | | Grade 3:15 |
| Tongue | Squamous cell carcinoma | 44 | | Grade 1:8 |
| | | | | Grade 2:24 |
| | | | | Grade 3:12 |
| Penis | Squamous cell carcinoma | 6 | | Grade 1:2 |
| | | | | Grade 2:3 |
| | | | | Grade 3:1 |
| Pancreas | Adenocarcinoma | 26 | Oncocytic: 1 (no grade assigned) | Grade 1:8 |
| | | | 1 adenosquamous | Grade 2:11 |
| | | | 1 undifferentiated | Grad3 3:5 |
| | | | | Grade 4:1 |
| Small intestine | Adenocarcinoma | 19 | | |
| Various sites | Neuroendocrine carcinoma | 25 | | Grade 1:15 |
| | | | | Grade 2:2 |
| | | | | Grade 3:8 |

Figure 5

Confusion Matrices and Accuracies for Training, Independent, and Institutional Independent Test Sets

Training–Test Split

| Urothelial | Squamous | Adenocarcinoma | Neuroendocrine |
|---|---|---|---|
| 25 | 4 | 1 | 0 |
| 3 | 26 | 0 | 0 |
| 0 | 0 | 29 | 1 |
| 0 | 1 | 1 | 9 |

CM Accuracy = 89%

Independent Test Set

| Urothelial | Squamous | Adenocarcinoma |
|---|---|---|
| 25 | 4 | 1 |
| 3 | 25 | 1 |
| 0 | 0 | 29 |

CM Accuracy = 88%

Institution Independent Test Set

| Urothelial | Squamous | Adenocarcinoma | Neuroendocrine |
|---|---|---|---|
| 19 | 1 | 0 | 0 |
| 9 | 11 | 0 | 0 |
| 2 | 0 | 16 | 0 |
| 0 | 5 | 0 | 14 |

CM Accuracy = 78%

Note no neuroendocrine samples were available from the expO dataset for the initial independent validation.

Figure 6

Confusion Matrices and Accuracies for the Training and Independent Test Sets for the Three Second Tier Primary Site of Origin Classifiers

Adenocarcinoma
Train–Test Split

| Kidney | Ovary | Uterus | Colon | Lung | Prostate | Breast |
|---|---|---|---|---|---|---|
| 19 | 0 | 0 | 0 | 0 | 1 | 0 |
| 1 | 9 | 9 | 0 | 0 | 0 | 1 |
| 0 | 4 | 14 | 0 | 0 | 0 | 2 |
| 0 | 0 | 0 | 20 | 0 | 0 | 0 |
| 0 | 0 | 0 | 0 | 20 | 0 | 0 |
| 0 | 0 | 1 | 0 | 0 | 19 | 0 |
| 0 | 1 | 1 | 0 | 0 | 0 | 17 |

CM Accuracy = 84%

Independent Test Set

| Kidney | Ovary | Uterus | Colon | Lung | Prostate | Breast |
|---|---|---|---|---|---|---|
| 8 | 0 | 2 | 0 | 0 | 0 | 0 |
| 0 | 10 | 0 | 0 | 0 | 0 | 0 |
| 3 | 0 | 6 | 1 | 0 | 0 | 0 |
| 0 | 0 | 1 | 8 | 1 | 0 | 0 |
| 0 | 0 | 0 | 0 | 10 | 0 | 0 |
| 0 | 0 | 0 | 1 | 0 | 9 | 0 |
| 0 | 0 | 0 | 0 | 0 | 0 | 10 |

CM Accuracy = 87%

Squamous
Train–Test Split

| Tongue-larynx | Vulva | Cervix | Penis | Lung | Anal-rectum |
|---|---|---|---|---|---|
| 24 | 0 | 1 | 0 | 0 | 0 |
| 0 | 3 | 0 | 0 | 0 | 0 |
| 2 | 0 | 6 | 0 | 1 | 0 |
| 4 | 1 | 0 | 0 | 0 | 0 |
| 1 | 0 | 1 | 0 | 16 | 0 |
| 0 | 0 | 0 | 0 | 0 | 8 |

CM Accuracy = 83%

Independent Test Set

| Tongue-larynx | Vulva | Cervix | Penis | Lung | Anal-rectum |
|---|---|---|---|---|---|
| 11 | 0 | 0 | 0 | 0 | 0 |
| 2 | 0 | 0 | 0 | 0 | 0 |
| 0 | 0 | 6 | 0 | 0 | 0 |
| 0 | 0 | 0 | 1 | 1 | 0 |
| 0 | 0 | 0 | 0 | 4 | 0 |
| 0 | 0 | 0 | 0 | 0 | 4 |

CM Accuracy = 90%

Neuroendocrine
Train–Test Split

| Small-bowel | Pancreas | Lung |
|---|---|---|
| 9 | 0 | 2 |
| 0 | 7 | 0 |
| 0 | 0 | 11 |

CM Accuracy = 93%

Independent Test Set

| Small-bowel | Pancreas | Lung |
|---|---|---|
| 4 | 0 | 1 |
| 0 | 4 | 0 |
| 0 | 0 | 11 |

CM Accuracy = 87%

Samples from the Moffitt and expO data sets were first grouped and tumors randomly selected for both training and independent validation.

Figure 7

Set of Genes Differentially Expressed among the Four Carcinoma Types

| Tumor type | Gene title | Gene symbol |
|---|---|---|
| Adenocarcinoma | Hexokinase domain containing 1 | HKDC1 |
| | KIAA0152 | KIAA0152 |
| | Calmodulin-like 4 | CALML4 |
| | Amiloride binding protein 1 (amine oxidase [copper-containing]) | ABP1 |
| | Tripartite motif-containing 15 | TRIM15 |
| | Hepatocyte nuclear factor 4, gamma | HNF4G |
| | Crystallin, lambda 1 | CRYL1 |
| Neuroendocrine | Yes-associated protein 1, 65 kDa | YAP1 |
| | Kinesin family member 1A | KIF1A |
| | Suppression of tumorigenicity 18 (breast carcinoma; zinc finger protein) | ST18 |
| | Synaptic vesicle glycoprotein 2A | SV2A |
| | Cartilage associated protein | CRTAP |
| | Absent in melanoma 1 | AIM1 |
| | Tumor necrosis factor receptor superfamily, member 10b | TNFRSF10B |
| | Leucine zipper protein 1 | LUZP1 |
| Squamous | S100 calcium binding protein A16 | S100A16 |
| | Ribosomal protein L39-like | RPL39L |
| | Hypothetical protein MGC35402 | MGC35402 |
| | Lysosomal-associated membrane protein 3 | LAMP3 |
| | Keratin 5 (epidermolysis bullosa simplex, Dowling-Meara/Köbner/Weber-Cockayne types) | KRT5 |
| | ATP-binding cassette, sub-family A (ABC1), member 13 | ABCA13 |
| | Pleckstrin homology domain containing, family A member 6 | PLEKHA6 |
| Urothelial | Similar to OK/SW-CL.16 | LOC440552 |
| | Desmocollin 3 | DSC3 |
| | Interferon, gamma-inducible protein 16 | IFI16 |
| | Rho GTPase activating protein 23 | ARHGAP23 |
| | GATA binding protein 3 | GATA3 |
| | Dehydrogenase/reductase (SDR family) member 2 | DHRS2 |
| | Leucine-rich repeats and immunoglobulin-like domains 1/leucine-rich repeats and immunoglobulin-like domains 1 | LRIG1 |
| | Sema domain, transmembrane domain (TM), and cytoplasmic domain, (semaphorin) 6D | SEMA6D |
| | Hypothetical protein LOC203274 | LOC203274 |
| | Ceramide kinase | CERK |

Figure 8

| NEUROENDOCRINE | | |
|---|---|---|
| Affymetrix Probeset ID | Gene Symbol | Gene Title |
| 200885_at | RHOC | ras homolog gene family, member C |
| 201367_s_at | ZFP36L2 | zinc finger protein 36, C3H type-like 2 |
| 201804_x_at | CKAP1 | cytoskeleton associated protein 1 |
| 204272_at | LGALS4 | lectin, galactoside-binding, soluble, 4 (galectin 4) |
| 208709_s_at | NRD1 | nardilysin (N-arginine dibasic convertase) |
| 210505_at | ADH7 | alcohol dehydrogenase 7 (class IV), mu or sigma polypeptide |
| 212534_at | ZNF24 | Zinc finger protein 24 (KOX 17) |
| 212916_at | PHF8 | PHD finger protein 8 |
| 214027_x_at | DES /// FAM48A | desmin /// family with sequence similarity 48, member A |
| 215195_at | PRKCA | protein kinase C, alpha |
| 216194_s_at | CKAP1 | cytoskeleton associated protein 1 |
| 218143_s_at | SCAMP2 | secretory carrier membrane protein 2 |
| 219150_s_at | CENTA1 | centaurin, alpha 1 |
| 219496_at | C2orf26 | chromosome 2 open reading frame 26 |
| 219805_at | FLJ22965 | hypothetical protein FLJ22965 |
| 220465_at | FLJ12355 | hypothetical protein FLJ12355 |
| 220538_at | ADM2 | adrenomedullin 2 |
| 221715_at | MYST3 | MYST histone acetyltransferase (monocytic leukemia) 3 /// MYST histone acetyltransferase (monocytic leukemia) 3 |
| 90265_at | CENTA1 | centaurin, alpha 1 |
| 91826_at | EPS8L1 | EPS8-like 1 |
| 223946_at | CRSP3 | cofactor required for Sp1 transcriptional activation, subunit 3, 130kDa |
| 224026_at | --- | --- |
| 224257_s_at | PBOV1 | prostate and breast cancer overexpressed 1 |
| 225975_at | PCDH18 | protocadherin 18 |
| 225977_at | PCDH18 | protocadherin 18 |
| 226134_s_at | MSI2 | Musashi homolog 2 (Drosophila) |
| 226514_at | ZNF71 | zinc finger protein 71 (Cos26) |
| 227481_at | CNKSR3 | CNKSR family member 3 |
| 227818_at | CCDC21 | coiled-coil domain containing 21 |
| 229783_at | AKAP13 | A kinase (PRKA) anchor protein 13 |
| 230188_at | ICHTHYIN | ichthyin protein |
| 231284_at | --- | --- |
| 233696_at | VPS37C | Vacuolar protein sorting 37C (yeast) |
| 233763_at | ANKRD6 | Ankyrin repeat domain 6 |
| 234516_at | IL1R1 | Interleukin 1 receptor, type I |
| 235679_at | ELA2A | Elastase 2A |
| 236054_at | --- | --- |
| 236765_at | --- | Transcribed locus, moderately similar to NP_777603.1 hypothetical protein FLJ25976 [Homo sapiens] |
| 237623_at | --- | MRNA; cDNA DKFZp686L04236 (from clone DKFZp686L04236) |
| 237982_at | LOC151363 | hypothetical LOC151363 |
| 238251_at | --- | Transcribed locus |
| 239079_at | --- | Transcribed locus |
| 240381_at | LOC58486 | Transposon-derived Buster1 transposase-like protein gene |
| 241262_at | --- | --- |
| 241879_at | --- | Transcribed locus |
| 242132_x_at | --- | --- |
| 243434_at | FLJ10874 | Chromosome 1 open reading frame 75 |
| 244271_at | --- | Transcribed locus, weakly similar to NP_872301.1 hypothetical protein FLJ25224 [Homo sapiens] |
| 244537_at | HIP2 | Huntingtin interacting protein 2 |
| 1557121_s_at | ABC1 | Amplified in breast cancer 1 |

Figure 9

| SQUAMOUS Affymetrix Probeset ID | Gene Symbol | Gene Title |
|---|---|---|
| 201026_at | EIF5B | eukaryotic translation initiation factor 5B |
| 201667_at | GJA1 | gap junction protein, alpha 1, 43kDa (connexin 43) |
| 201733_at | CLCN3 | chloride channel 3 |
| 205190_at | PLS1 | plastin 1 (I isoform) |
| 206775_at | CUBN | cubilin (intrinsic factor-cobalamin receptor) |
| 207592_s_at | HCN2 | hyperpolarization activated cyclic nucleotide-gated potassium channel 2 |
| 209810_at | SFTPB | surfactant, pulmonary-associated protein B |
| 210443_x_at | OGFR | opioid growth factor receptor |
| 210918_at | --- | --- |
| 212309_at | CLASP2 | cytoplasmic linker associated protein 2 |
| 212477_at | CENTB2 | centaurin, beta 2 |
| 213288_at | OACT2 | O-acyltransferase (membrane bound) domain containing 2 |
| 214052_x_at | XTP2 | BAT2 domain containing 1 |
| 217661_x_at | SIX5 | sine oculis homeobox homolog 5 (Drosophila) |
| 218327_s_at | SNAP29 | synaptosomal-associated protein, 29kDa |
| 218509_at | LPPR2 | lipid phosphate phosphatase-related protein type 2 |
| 218835_at | SFTPA2 | surfactant, pulmonary-associated protein A2 |
| 219051_x_at | METRN | meteorin, glial cell differentiation regulator |
| 219916_s_at | RNF39 | ring finger protein 39 |
| 219992_at | TAC3 | tachykinin 3 (neuromedin K, neurokinin beta) |
| 220096_at | RNASET2 | ribonuclease T2 |
| 221794_at | DOCK6 | dedicator of cytokinesis 6 |
| 55583_at | DOCK6 | dedicator of cytokinesis 6 |
| 55705_at | C19orf22 | chromosome 19 open reading frame 22 |
| 222936_s_at | C1orf121 | chromosome 1 open reading frame 121 |
| 223806_s_at | NAPSA | napsin A aspartic peptidase |
| 225258_at | FBLIM1 | filamin binding LIM protein 1 |
| 225289_at | STAT3 | signal transducer and activator of transcription 3 (acute-phase response factor) |
| 225702_at | C8orf76 | chromosome 8 open reading frame 76 |
| 227142_at | PLEKHG5 | pleckstrin homology domain containing, family G (with RhoGef domain) member 5 |
| 227379_at | OACT1 | O-acyltransferase (membrane bound) domain containing 1 |
| 227848_at | PEBP4 | phosphatidylethanolamine-binding protein 4 |
| 228477_at | FLJ10154 | Hypothetical protein FLJ10154 |
| 228634_s_at | --- | Similar to cold shock domain protein A; Cold-shock domain protein A |
| 230219_at | NDE1 | nudE nuclear distribution gene E homolog 1 (A. nidulans) |
| 231011_at | FLJ10378 | La ribonucleoprotein domain family, member 2 |
| 233523_at | C20orf186 | chromosome 20 open reading frame 186 |
| 233959_at | LOC221442 | hypothetical protein LOC221442 |
| 234789_at | --- | CDNA FLJ12051 fis, clone HEMBB1002005 |
| 234794_at | SHB | Src homology 2 domain containing adaptor protein B |
| 236934_at | IGF1R | Insulin-like growth factor 1 receptor |
| 237568_at | MSCP | Solute carrier family 25, member 37 |
| 240765_at | HCMOGT-1 | Spectrin domain with coiled-coils 1 |
| 242011_at | --- | --- |
| 1553749_at | FAM76B | family with sequence similarity 76, member B |
| 1559298_a_at | FLJ42289 | FLJ42289 protein |
| 1559311_at | EHMT1 | Euchromatic histone-lysine N-methyltransferase 1 |
| 1561692_at | WWOX | WW domain containing oxidoreductase |
| 1569157_s_at | LOC162993 | hypothetical protein LOC162993 |
| 1569303_s_at | RGS20 | regulator of G-protein signalling 20 |

Figure 10

ADENOCARCINOMA

| Affymetrix Probeset ID | Gene Symbol | Gene Title |
|---|---|---|
| 202016_at | MEST | mesoderm specific transcript homolog (mouse) |
| 202457_s_at | PPP3CA | protein phosphatase 3 (formerly 2B), catalytic subunit, alpha isoform (calcineurin A alpha) |
| 204069_at | MEIS1 | Meis1, myeloid ecotropic viral integration site 1 homolog (mouse) |
| 204582_s_at | KLK3 | kallikrein 3, (prostate specific antigen) |
| 204653_at | TFAP2A | transcription factor AP-2 alpha (activating enhancer binding protein 2 alpha) |
| 205670_at | GAL3ST1 | galactose-3-O-sulfotransferase 1 |
| 205674_x_at | FXYD2 | FXYD domain containing ion transport regulator 2 |
| 206022_at | NDP | Norrie disease (pseudoglioma) |
| 206067_s_at | WT1 | Wilms tumor 1 |
| 206418_at | NOX1 | NADPH oxidase 1 |
| 207217_s_at | NOX1 | NADPH oxidase 1 |
| 207434_s_at | FXYD2 | FXYD domain containing ion transport regulator 2 |
| 209570_s_at | D4S234E | DNA segment on chromosome 4 (unique) 234 expressed sequence |
| 209604_s_at | GATA3 | GATA binding protein 3 |
| 209692_at | EYA2 | eyes absent homolog 2 (Drosophila) |
| 209810_at | SFTPB | surfactant, pulmonary-associated protein B |
| 209847_at | CDH17 | cadherin 17, LI cadherin (liver-intestine) |
| 209855_s_at | KLK2 | kallikrein 2, prostatic |
| 210239_at | IRX5 | iroquois homeobox protein 5 |
| 210289_at | NAT8 | N-acetyltransferase 8 (camello like) |
| 210302_s_at | MAB21L2 | mab-21-like 2 (C. elegans) |
| 210808_s_at | NOX1 | NADPH oxidase 1 |
| 211024_s_at | TITF1 | thyroid transcription factor 1 /// thyroid transcription factor 1 |
| 212136_at | ATP2B4 | ATPase, Ca++ transporting, plasma membrane 4 |
| 212231_at | FBXO21 | F-box protein 21 |
| 212909_at | LYPD1 | LY6/PLAUR domain containing 1 |
| 212960_at | KIAA0882 | KIAA0882 protein |
| 213036_x_at | ATP2A3 | ATPase, Ca++ transporting, ubiquitous |
| 213936_x_at | SFTPB | surfactant, pulmonary-associated protein B |
| 218640_s_at | PLEKHF2 | pleckstrin homology domain containing, family F (with FYVE domain) member 2 |
| 218687_s_at | MUC13 | mucin 13, epithelial transmembrane |
| 219993_at | SOX17 | SRY (sex determining region Y)-box 17 |
| 221424_s_at | OR51E2 | olfactory receptor, family 51, subfamily E, member 2 /// olfactory receptor, family 51, subfamily E, member 2 |
| 37004_at | SFTPB | surfactant, pulmonary-associated protein B |
| 222712_s_at | MUC13 | mucin 13, epithelial transmembrane |
| 227075_at | ELP3 | elongation protein 3 homolog (S. cerevisiae) |
| 227629_at | PRLR | Prolactin receptor |
| 228377_at | KLHL14 | kelch-like 14 (Drosophila) |
| 228546_at | DPP6 | dipeptidylpeptidase 6 |
| 228782_at | SCGB3A2 | secretoglobin, family 3A, member 2 |
| 228979_at | LOC253970 | hypothetical protein LOC253970 |
| 230896_at | CCDC4 | coiled-coil domain containing 4 |
| 230943_at | SOX17 | SRY (sex determining region Y)-box 17 |
| 231315_at | TITF1 | Thyroid transcription factor 1 |
| 231790_at | DMGDH | dimethylglycine dehydrogenase |
| 235774_at | LOC553137 | hypothetical LOC553137 |
| 236545_at | PPP3CA | Protein phosphatase 3 (formerly 2B), catalytic subunit, alpha isoform (calcineurin A alpha) |
| 237077_at | ACPP | Acid phosphatase, prostate |
| 237328_at | --- | Transcribed locus |
| 244579_at | TRPS1 | Trichorhinophalangeal syndrome I |

Figure 11

HYBRID MODEL FOR THE CLASSIFICATION OF CARCINOMA SUBTYPES

CROSS REFERENCE TO RELATED APPLICATIONS

This application is a continuation of and claims priority to International Patent Application No. PCT/US11/29208, entitled "HYBRID MODEL FOR THE CLASSIFICATION OF CARCINOMA SUBTYPES," filed on Mar. 21, 2011, which is a non-provisional of and claims priority to U.S. Provisional Application No. 61/315,726 filed Mar. 19, 2010, with the same title, the contents of which are hereby incorporated by reference into this disclosure.

STATEMENT OF GOVERNMENT SUPPORT

This invention was made with government support under Grant No. CA112215, awarded by the National Institutes of Health (NIH). The government has certain rights in the invention.

FIELD OF INVENTION

This invention relates to methods of identifying unknown tumors. Specifically, the invention provides a hybrid method using immunohistochemistry and gene expression analysis to identify unknown site of origin malignancies.

BACKGROUND OF THE INVENTION

Carcinoma of unknown primary (CUP) is estimated to consist of about 3-5% of all metastatic cancers, with the American Cancer Society estimating in 2010 that there were 30,680 new cases of CUP and 44,030 deaths resulting from CUP. The diagnosis of CUP requires a biopsy-proven metastatic malignancy and no identifiable primary tumor after a thorough clinical evaluation. For cases which are designated as CUP after this evaluation, the source of these tumors is identified in between only about 20% to about 30% of the time ante mortem. The prognosis for patients in whom a primary site has not been identified is poor, with the median survival ranging from about 2 months to about 10 months. (Monzon F A, et al. Diagnosis of Metastatic Neoplasms. Arch Pathol Lab Med. 2010, 134:216-224).

Identifying site of primary origin for CUP remains a challenge for the pathologist, even with modern pathological techniques. This carries serious implications for cancer therapy, as current oncological therapeutic regimes are targeted to site of origin. Microarray based gene expression studies are one potential technological solution to this problem, and the feasibility of this methodology for broad-based tumor classification has been established by a number of studies. (Bloom, et al.; Multi-platform, multi-site, microarray-based human tumor classification, Am J Pathol 2004, 164:9-16; Bridgewater, et al., Gene expression profiling may improve diagnosis in patients with carcinoma of unknown primary, Br J Cancer 2008, 98:1425-1430; Buckhaults, et al., Identifying tumors origin using a gene expression-based classification map, Cancer Res 2003, 63:4144-4149. Giordano, et al., Organ-specific molecular classification of primary lung, colon, and ovarian adenocarcinomas using gene expression profiles, Am J Pathol 2001, 159:1231-1238; Ma, et al., Molecular classification of human cancers using a 92-gene real-time quantitative polymerase chain reaction assay. Arch Pathol Lab Med 2006, 130:465-473; Ramaswamy, et al., Multiclass cancer diagnosis using tumor gene expression signatures, Proc Natl Acad Sci USA 2001, 98:15149-15154; Su et al., Molecular classification of human carcinomas by use of gene expression signatures. Cancer Res 2001, 61:7399-7393) Approaches based entirely on gene expression data however, limit these studies, because they do not take into account well understood differences in morphology and biological differentiation. Pathologists recognize and exploit these differences in their daily practice.

The prior art in the area of diagnostic tests for determining site of primary origin of CUP fail to take into account differences in morphology and biological differentiation. Two tests are commercially available in the United States, the Pathwork Tissue of Origin Test (Pathwork Diagnostics, Sunnyvale, Calif.) and the THEROS CancerTYPe ID by bioTheranostics San Diego, Calif.). Both of these are mRNA-based products. The Pathwork Tissue of Origin Test issues a similarity score for 15 tumor types using a 1550-gene profile that uses the expression level of 1550 transcripts to perform pair-wise comparison between the test sample and each of the 15 tissues on the test panel. A validation study of this test was performed using 547 frozen specimens submitted from four institutions. The tissues were derived from either metastatic cancers or poorly of undifferentiated primary cancers. The test showed a sensitivity of 87.8% and a specificity of 99.4%. (Monzon F A et al. Multicenter validation of a 1,550-gene expression profile for identification of tumor tissue of origin. J Clin Oncol. 2009, 27:2503-2508) A limitation of this validation study is that it was performed using frozen tissues. This validation study is significant because it focused on poorly differentiated or undifferentiated primary carcinomas and metastatic carcinomas, which are the real challenges in tumor diagnosis. The Pathwork Tissue of Origin Test has now been developed for use in formalin-fixed, paraffin-embedded (FFPE) tissues as the PathChip. In a study of 462 FFPE specimens, the test demonstrated 89% positive percent agreement with available diagnoses, and greater than 99% negative percent agreement in specimens that had previously been identified with existing methods as being among the 15 tumor types on the panel. (Pillai R. et al. A microarray based gene expression test as an aid to tumor diagnosis using formalin-fixed paraffin-embedded (FFPE) specimens. Pathwork Diagnostics. Abstracts and Case Studies from the College of American Pathologists, 2009 Annual Meeting. Arch Pathol Lab Med 2009, 133:1608-1716). While identifying up to 15 tumor types, most may be distinguished with the application of simple ancillary studies, such as flow cytometry and gene rearrangement studies to diagnose non-Hodgkin lymphoma and immunohistochemistry to diagnose melanomas. Some of the recognized primaries, such as colorectal primaries and breast, have established immunohistochemical patterns. While this test may be helpful for the tumor types that do not have a well-defined immunohistochemical pattern or are poorly differentiated or undifferentiated, it does not report on differences in tumor morphology, such as squamous cell carcinoma versus adenocarcinoma versus neuroendocrine carcinoma. These features are more important in predicting cancer therapy and prognosis.

The THEROS CancerTYPE ID is designed to focus on those cases that are indeterminate and distinguishes among 39 tumor types. Included in these 39 tumor types are epithelial malignancies, lymphomas, mesotheliomas, meningiomas, stromal neoplasms, and pheochromocytoma. This test provides information regarding tumor subtype and separating squamous cell carcinomas from adenocarcinomas for certain primary sites, however the test uses an "all-encompassing" approach to tumor classification. Many of these separations are coarse distinctions that may be accomplished with the use of widely-available immunohistochemistry. For example, lymphomas may be distinguished from carcinomas with the use of immunohistochemical antibodies for cytokaratins and LCA and even finer distinctions may routinely be made with additional ancillary testing. For example, current practice is to use flow cytometry and gene rearrangement studies to subclassify non-Hodgkin's lymphoma. Mutations in the CKIT gene or PDGFR gene are diagnostic for gastrointestinal stromal tumors. This approach is useful for the undifferentiated neoplasms, in which a primary line of differentiation cannot be determined. It is noteworthy that while the test was evaluated on an independent sample set, this set had only 119 tumors to represent 30 tumor classes. Representation from each tumor type ranged from between 1 and 10 specimens, with 18 tissue types being represented by 3 samples or less, thus the reported sensitivity and specificity for a specific tumor type may only reflect the correct classification of 1 specimen. (Monzon F A, et al. Diagnosis of Metastatic Neoplasms. Arch Pathol Lab Med. 2010, 134:216-224)

The Veridex CUP assay (Raritan, N.J.) uses 10 genes tested by RT-PCR to distinguish among six different primary sites of carcinoma: lung, breast, colon, ovary, pancreas, and prostate. (Varadhachary G R, et al. Molecular profiling of carcinoma of unknown primary and correlation with clinical evaluation. J Clin Oncol 2008, 26:4442-4448; Talantov D, et al. A quantitative reverse transcriptase-polymerase chain reaction assay to identify metastatic carcinoma tissue of origin. J Mol Diagn 2006, 8:320-329) Although these studies demonstrate the feasibility of this assay, the assay itself left 48% of patients unassigned to an origin.

The CupPrint classifier, being developed by Agendia (Amsterdam, Netherlands), focuses on a finer distinction for adenocarcinoma of unknown primary. (Horlings H M, et al. gene expression profiling to identify the histogenic origin of metastatic adenocarcinomas of unknown primary. J Clin Oncol 2008, 26:4435-4441; van Laar R K, et al. Implementation of a novel microarray-based diagnostic test for cancer of unknown primary. Int J Cancer 2009, 125:1390-1397). The CupPrint classifier is developed by using the databases from another published classifier. (Ma X J, et al. Molecular classification of human cancers using a 92-gene real-time quantitative polymerase chain reaction assay. Arch Pathol Lab Med. 2006, 130:465-473). This is an RT-PCR based test applicable to formalin-fixed paraffin-embedded tissue. It is a customized eight-pack microarray containing 495 genes that were selected as highly differentiated expressed between 48 tumor types. A weighted five-nearest neighbor algorithm was used to determine the five most molecularly similar tumors in the database. They achieved an accuracy of 83% for carcinomas with a known primary and 94% for a carcinoma of unknown primary. This study focused mostly on adenocarcinomas, although urothelial carcinomas of the scheme. The classifier of this system had a systematic problem in classifying lung and pancreatic carcinomas, misclassifying respectively 63% and 100% of these carcinomas. No satisfactory explanation for this problem is provided. This limitation is important because these two primary sites most often give rise to adenocarcinoma of unknown primary.

Another previous microarray-based gene expression study proposed a tumor classifier based on a pathological treebased framework using a schema in which neoplasms were separated in a sequential coarse to fine approach, beginning with the separation of solid malignancies from hematolymphoid malignancies. (Shedden, et al., Accurate molecular classification of human cancers based on gene expression using a simple classifier with a pathological tree-based framework, Am J Pathol 2003, 163:1985-1995) The authors further refined the epithelial malignancies into those of Mullerian (ovarian, endometrial) and non-Mullerian origin (breast, prostate, lung, colon, bladder, renal, pancreas). This approach more realistically organizes tumor classification to fit within a pathologist-based diagnostic algorithm. However, the test leaves out the first step typically performed by pathologists, the recognition of morphological subtypes of carcinomas, which include squamous cell carcinomas, urothelial carcinomas, adenocarcinomas, and neuroendocrine carcinomas.

Previous studies have focused solely on identifying site of primary origin for adenocarcinoma, proving the effectiveness of using gene expression to classify tumors within specific pathological carcinoma subtypes. (Buckhaults, et al., Identifying tumor origin using a gene expression-based classification map, Cancer Res 2003, 63:4144-4149; Giordano, et al., Organ-specific molecular classification of primary lung, colon, and ovarian adenocarcinomas using gene expression profiles, Am J Pathol 2001, 159:1231-1238; Dennis et al., Identification from public data of molecular markers of adenocarcinoma characteristic of the site of origin, Cancer Res 2002, 62:5999-6005) Molecular classifiers for site of primary origin for squamous cell carcinoma and neuroendocrine carcinomas have not been developed. One study mentioned an attempt at classifying squamous cell carcinoma of unknown primary and reported no success. (Tothill, et al., An expression-based site of origin diagnostic method designed for clinical application to cancer of unknown origin, Cancer Res 2005, 65:4031-4040) Two studies have focused on a very specific differential diagnosis; distinguishing pulmonary from head and neck primary squamous cell carcinomas. One study developed using a classifier based on the Affymetrix HG_U95Av2 oligonucleotide microarray, which focused specifically on separating lung from tongue squamous cell carcinomas (Talbot, et al., Gene expression profiling allows distinction between primary and metastatic squamous cell carcinomas in the lung, Cancer Res 2005, 65:3063-3071). Another study developed a 10-gene classifier derived from Affymetrix U133 and HG_U95Av2 data with 96% accuracy (Vachani, et al., A 10-gene classifier for distinguishing head and neck squamous cell carcinoma and lung squamous cell carcinoma, Clin Cancer Res 2007, 13:2905-2915). Neither of these studies presented a molecular classifier for neuroendocrine carcinoma of unknown primary.

The prior art also includes a miRNA classifier developed for carcinoma tissue origin by Rosetta Genomics (Rehovot, Israel). (Rosenfield N, et al. MicroRNAs accurately identify cancer tissue origin. Nature Biotechnol 2008, 26:462-469). This classifier uses a binary tree method of classification going from coarse to fine specifications. The decision at each node is a simple binary decision that can be performed using the expression levels of a few miRNAs. This classifier was tested on 400 paraffin-embedded and frozen samples from 22 different primary and metastatic tumor tissues. Overall accuracy was >90%. Accuracy for the test reached 89% in an independent data set. The approach described in this article is based on tumor cell differentiation, similar to the approach used by Shedden, (Shedden K A, et al. Accurate molecular classification of human cancers based on gene expression using a simple classifier with a pathological tree-based framework. Am J Pathol 2003, 163:1985-1995) The approach starts with the distinction of neuroendocrine from aquamous and glandular carcinomas. This study validates the approach of the present inventors in that separate miRNAs distinguish among squamous cell and adenocarcinoma of the lung. Carcinoid of the lung is recognized as distinct from other malignancies of the lung.

The present invention overcomes the shortcomings of the prior art by utilizing a pathology-based approach to tumor classification. The approach follows the algorithmic hierarchy used by pathologists and can be directly compared to or integrated with the results of IHC staining. In use, the tumor is identified as a cytokeratin-positive carcinoma and subsequently subclassified into one of four basic types adenocarcinoma, squamous cell carcinoma, neuroendocrine carcinoma, and urothelial carcinoma. This subclassification is follow by the prediction of site of origin based on second tier gene expression classifiers.

SUMMARY OF INVENTION

A novel hybrid diagnostic for the identity of the site of origin of carcinoma unknown primary (CUP) that integrate a hierarchy of gene expression classifiers into the algorithmic method used with IHC is presented. Identification of the site of origin for CUP remains a challenge for modern pathology, and correct diagnosis is critical to determining the most efficacious treatment for the patient. Standard pathological approaches combine morphology and IHC studies to first identify cytokeratin-positive carcinomas and then subclassify them into adenocarcinoma, squamous cell carcinoma, neuroendocrine carcinoma, and urothelial carcinoma. Subsequently, organ-specific IHC-markers, if available, are used to assign the tumor's primary site of origin. Previous gene expression classifiers have shown promise in tumor classification but cannot readily be integrated into standard practice because they ignore the algorithmic hierarchy used in pathologist. This approach however, follows the standard work flow used in the everyday practice pathology, and can be directly compared with or integrated with the results of IHC staining. In this method, a tumor is initially assigned to one of the carcinoma subclasses by the top tier expression classifier. Then second tier gene expression classifiers are used to assign the site of origin, resulting in both carcinoma subtype and primary site classification.

In a first embodiment, a method of identifying the origin of a neoplasm of unknown primary is presented. The method is comprised of: obtaining a sample of a neoplasm; obtaining morphological data of the neoplasm; obtaining cytokeratin immunohistochemical data of the neoplasm; developing microarray-based gene expression classifiers for the neoplasm; and correlating the morphological data, immunohistochemical data, and microarray-based gene expression to the tissue origin of the neoplasm. The method can be further comprised of: performing immunohistochemistry on cytokeratin positive neoplasms to differentiate between carcinoma, mesothelioma and germ cell tumors; performing immunohistochemistry on carcinomas; and comparing the immunohistochemistry data from the carcinomas to the microarray-based gene expression.

The gene expression classifiers can be arranged in a hierarchy that is comprised of top tier classifiers and second tier classifiers. The top tier classifiers can be assigned to one of four subclasses of carcinomas: squamous cell carcinoma, urothelial carcinoma, neuroendocrine carcinoma, and adenocarcinoma.

The top tier classifiers for adenocarcinoma can be selected from the group consisting of HKDC1, KIAA0152, CALML4, ABP1, TRIM15, HNF4G, and CRYL1. In an embodiment, the top tier classifier for adenocarcinoma can HNF4.

The top tier classifiers for neuroendocrine carcinoma can be selected from the group consisting of YAP1, KIF1A, ST18, SV2A, CRTAP, AIM1, TNFFRSF10B, LUZP1, and S100A16. In an embodiment, the top tier classifier for neuroendocrine carcinoma can be SV2.

The top tier classifiers for squamous cell carcinoma can be selected from the group consisting of RPL39L, MGC35402, LAMP3, KRT5, ABCA13, PLEKHA6, LOC440552, DSC3, and IFI16. In an embodiment, the top tier classifier for squamous cell carcinoma can be cytokeratin 5 or desmcollin-3.

The top tier classifiers for urothelial carcinoma can be selected from the group consisting of ARHGAP23, GATA3, DHRS2, LRIG1, SEMA6D, LOC203274, and CERK.

The second tier classifiers can be assigned to one of three subclasses of carcinomas selected from the group consisting of squamous cell carcinoma, neuroendocrine carcinoma, and adenocarcinoma to determine a primary site of origin of the tumor.

In another embodiment, a method of identifying the origin of a neoplasm of unknown primary is presented comprising: obtaining a sample of a neoplasm; obtaining morphological data of the neoplasm; obtaining cytokeratin immunohistochemical data of the neoplasm; obtaining microarray-based gene expression for the neoplasm; utilizing a top tier of gene expression classifiers to classify the neoplasm according to carcinoma type; utilizing a second tier of gene expression classifiers to classify the neoplasm according to primary site of origin. The method can be further comprised of performing immunohistochemistry on cytokeratin positive neoplasms to differentiate between carcinoma, mesothelioma, and germ cell tumors; performing immunohistochemistry on the carcinoma; and comparing the immunohistochemistry data from the carcinomas to the microarray-based gene expression to correlate the morphological data, the immunohistochemical data, and the microarray-based gene expression classifier data to the tissue origin of the neoplasm.

The top tier classifiers can be assigned to one of four subclasses of carcinomas selected from the group consisting of squamous cell carcinoma, urothelial carcinoma, neuroendocrine carcinoma, and adenocarcinoma.

The top tier classifiers for adenocarcinoma can be selected from the group consisting of HKDC1, KIAA0152, CALML4, ABP1, TRIM15, HNF4G, and CRYL1.

The top tier classifiers for neuroendocrine carcinoma can be selected from the group consisting of YAP1, KIF1A, ST18, SV2A, CRTAP, AIM1, TNFFRSF10B, LUZP1, and S100A16.

The top tier classifiers for squamous cell carcinoma can be selected from the group consisting of RPL39L, MGC35402, LAMP3, KRT5, ABCA13, PLEKHA6, LOC440552, DSC3, and IFI16.

The top tier classifiers for urothelial carcinoma can be selected from the group consisting of ARHGAP23, GATA3, DHRS2, LRIG1, SEMA6D, LOC203274, and CERK.

The second tier classifiers can be assigned to one of three subclasses of carcinomas selected from the group consisting of squamous cell carcinoma, neuroendocrine carcinoma, and adenocarcinoma to determine a primary site of origin of the tumor.

In a further embodiment, a method of identifying the origin of a neoplasm of unknown primary is presented comprising: obtaining a sample of a neoplasm; obtaining morphological data of the neoplasm; obtaining cytokeratin immunohistochemical data of the neoplasm; differentiating cytokeratin positive neoplasms into carcinoma, mesothelioma and germ cell tumors using immunohistochemistry; differentiating carcinomas using immunohistochemistry; obtaining microarray-based gene expression for the neoplasm; utilizing a top tier of gene expression classifiers to classify the neoplasm according to carcinoma type; utilizing a second tier of gene expression classifiers to classify the carcinoma according to primary site of origin; comparing the immunohistochemistry data from the carcinomas to the microarray-based gene expression classifier data to correlate the morphological data, the immunohistochemical data, and the microarray-based gene expression classifiers to the tissue origin of the neoplasm.

The top tier classifiers can be assigned to one of four subclasses of carcinomas selected from the group consisting of squamous cell carcinoma, urothelial carcinoma, neuroendocrine carcinoma, and adenocarcinoma.

The top tier classifiers for adenocarcinoma can be selected from the group consisting of HKDC1, KIAA0152, CALML4, ABP1, TRIM15, HNF4G, and CRYL1.

The top tier classifiers for neuroendocrine carcinoma can be selected from the group consisting of YAP1, KIF1A, ST18, SV2A, CRTAP, AIM1, TNFFRSF10B, LUZP1, and S100A16.

The top tier classifiers for squamous cell carcinoma can be selected from the group consisting of RPL39L, MGC35402, LAMP3, KRT5, ABCA13, PLEKHA6, LOC440552, DSC3, and IFI16.

The top tier classifiers for urothelial carcinoma can be selected from the group consisting of ARHGAP23, GATA3, DHRS2, LRIG1, SEMA6D, LOC203274, and CERK.

The second tier classifiers can be assigned to one of three subclasses of carcinomas selected front the group consisting of squamous cell carcinoma, neuroendocrine carcinoma, and adenocarcinoma to determine a primary site of origin of the tumor.

Another embodiment includes a method of determining the primary site of origin of a neoplasm comprising: providing a gene expression profile of a plurality of neoplasms wherein each neoplasm contains at least one biomarker; obtaining a sample of neoplasm from the subject; establishing a gene expression profile for the sample; comparing the gene expression profile for the sample to the protein expression profile of the plurality of neoplasms using an artificial neural network to determine a two tier hierarchy classification system; utilizing a top tier of gene expression classifiers to classify the neoplasm according to carcinoma type; and utilizing a second tier of gene expression classifiers to classify the carcinoma according to primary site of origin.

The method can be further comprised of detecting the presence of at least one biomarker from the gene expression profile of the plurality of neoplasms in the gene expression profile for the sample.

The gene expression profile for the sample can be compared to the gene expression profile of the plurality of neoplasms using a leave-k-out cross validation algorithm.

The gene expression profile can be comprised of genes selected from the group consisting of HKDC1, KIAA0152, CALML4, ABP1, TRIM15, HNF4G, CRYL1, YAP1, KIF1A, ST18, SV2A, CRTAP, AIM1, TNFFRSF10B, LUZP1, S100A16, RPL39L, MGC35402, LAMP3, KRT5, ABCA13, PLEKHA6, LOC440552, DSC3, IFI16, ARHGAP23, GATA3, DHRS2, LRIG1, SEMA6D, LOC203274, and CERK. All 32 genes may be used in the gene expression profile. Alternatively one of groups of the 32 genes may be used in the gene expression profile.

BRIEF DESCRIPTION OF THE DRAWINGS

For a fuller understanding of the invention, reference should be made to the following detailed description, taken in connection with the accompanying drawings, in which:

FIG. 4 is a table of the IGC data indicating the top primary sites per histological subtype.

FIG. 5 is a table of the histologic type and primary site of origin for specimens obtained from H. Lee Moffitt Cancer Center Tissue Procurement Facility.

FIG. 6 is a table of the confusion matrices and accuracies for Training, Independent, and Institutional Independent Test Sets.

FIG. 7 is a table of the confusion matrices and accuracies for the Training and Independent Test Sets for the three second tier primary site of origin classifiers.

FIG. 8 is a table of the set of genes differentially expressed among the four carcinoma types.

FIG. 9 is a table of the second tier genes that were used to differentiate neuroendocrine carcinoma.

FIG. 10 is a table of the second tier genes that were used to differentiate squamous cell carcinoma.

FIG. 11 is a table of the second tier genes that were used to differentiate adenocarcinoma.

DETAILED DESCRIPTION OF THE PREFERRED EMBODIMENT

Figure 1:
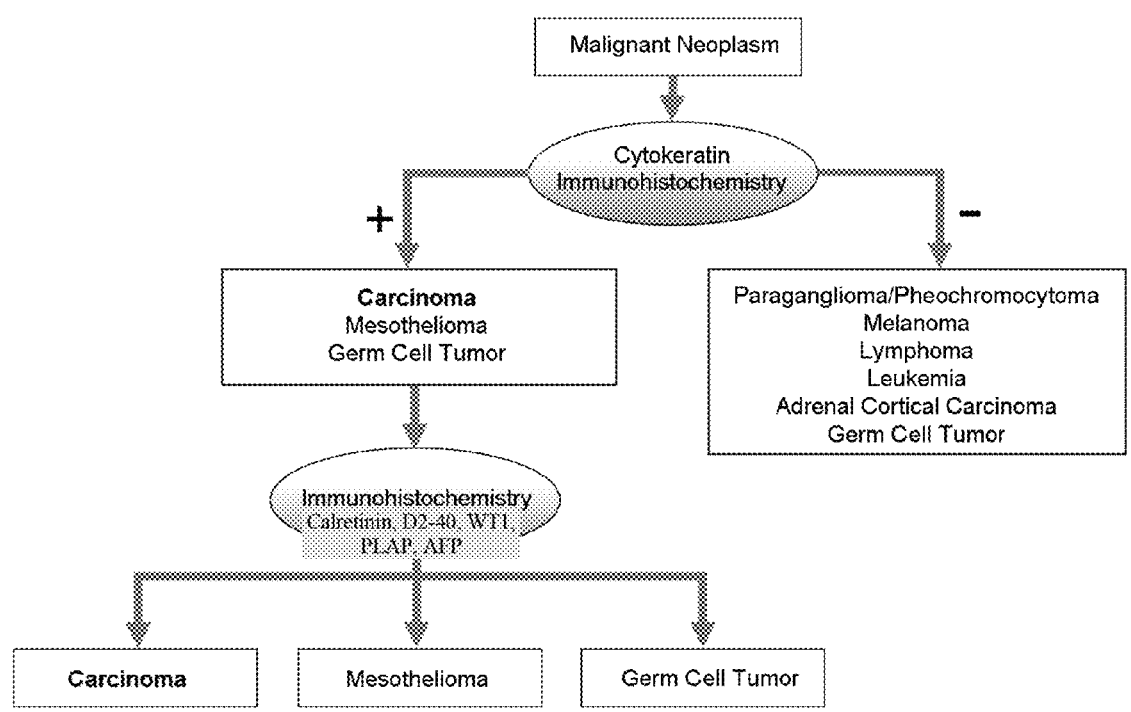
FIG. 1 is a diagram of IHC work flow for the identification of carcinoma from a malignant neoplasm. Initial Cytokeratin IHC separated the neoplasm into positive and negative for CK staining. A second panel of IHC delineates carcinoma from Mesothelioma and Germ Cell Tumors.

In the following detailed description of the preferred embodiments, reference is made to the accompanying drawings, which form a part hereof, and within which are shown by way of illustration specific embodiments by which the invention may be practiced. It is to be understood that other embodiments by which the invention may be practiced. It is to be understood that other embodiments may be utilized and structural changes may be made without departing from the scope of the invention.

The term "biomarker" is used herein to refer to a molecule whose level of nucleic acid or protein product has a quantitatively differential concentration or level with respect to an aspect of a biological state of a subject "Biomarker" is used interchangeably with "marker" herein. The level of the biomarker can be measured at both the nucleic acid level as well as the polypeptide level. At the nucleic acid level, a nucleic acid gene or a transcript which is transcribed from any part of the subject's chromosomal and extrachromosomal genome, including for example the mitochondrial genome, may be measured. Preferably an RNA transcript, more preferably an RNA transcript includes a primary transcript, a spliced transcript, an alternatively spliced transcript, or an mRNA of the biomarker is measured. At the polypeptide level a pre-propeptide, a propeptide, a mature peptide or a secreted peptide of the biomarker may be measured. A biomarker can be used either solely or in conjunction with one or more other identified biomarkers. Specific examples of biomarkers covered by the present invention include genes that are differentially expressed among carcinomas, specifically adenocarcinoma, neuroendocrine carcinoma, squamous cell carcinoma, and urothelial carcinoma. More specifically, biomarkers of the present invention include HKDC1, KIAA0152, CALML4, ABP1, TRIM15, HNF4G, CRYL1, YAP1, KIF1A, ST18, SV2A, CRTAP, AIM1, TNFFRSF10B, LUZP1, S100A16, RPL39L, MGC35402, LAMP3, KRT5, ABCA13, PLEKHA6, LOC440552, DSC3, IFI16, ARHGAP23, GATA3, DHRS2, LRIG1, SEMA6D, LOC203274, and CERK.

The term "expression level" as used herein refers to detecting the amount or level of expression of a biomarker of the present invention. The act of actually detecting the expression level of a biomarker refers to the act of actively determining whether a biomarker is expressed in a sample or not. This act can include determining whether the biomarker expression is upregulated, downregulated or substantially unchanged as compared to a control level expressed in a sample. The expression level in some cases may refer to detecting transcription of the gene encoding a biomarker protein and/or to detecting translation of the biomarker protein.

Expression of genes/transcripts and/or polypeptides encoded by the genes represented by the biomarkers of the present invention can be measured by any of a variety of methods known in the art. In general, expression of a nucleic acid molecule (e.g. RNA or DNA) can be detected by any suitable method or technique of measuring or detecting gene or polynucleotide sequence or expression. Such methods include, but are not limited to, polymerase chain reaction (PCR), reverse transcriptase PCR (RT-PCR), in situ PCR, qualitative PCR (q-PCR), in situ hybridization, Southern blot, Northern blot, sequence analysis, microarray analysis, detection of a reporter gene, or any other DNA/RNA hybridization platforms.

The term "quantifying" or "quantitating" when used in the context of quantifying transcription levels of a gene can refer to absolute or relative quantification. Absolute quantification can be achieved by including known concentration(s) of one or more target nucleic acids and referencing the hybridization intensity of unknowns with the known target nucleic acids (e.g. through the generation of a standard curve). Alternatively, relative quantification can be achieved by comparison of hybridization signals between two or more genes, or between two or more treatments to quantify the changes in hybridization intensity and, by implication transcription level.

The term "cell" or "cells" is used synonymously herein and refers to in vitro cultures of mammalian cells grown and maintained as known in the art, as well as biological samples obtained from tumor specimens or normal specimens in vivo.

The term "sample" as used herein refers to any physical sample that includes a cell or a cell extract from a cell, a tissue, or an organ including a biopsy sample. The sample can be from a biological source such as a subject or animal, or a portion thereof, or can be from a cell culture. Samples from a biological source can be from a normal or an abnormal organism, such as an organism known to be suffering from a condition or a disease state such as a neoplasm, or any portion thereof. Samples can also be from any fluid, tissue or organ including normal and abnormal (diseased or neoplastic) fluids tissue or organ. Samples from a subject or animal can be used in the present invention as obtained by the subject or animal and processed or cultured such that cells from the sample can be sustained in vitro as a primary or continuous cell culture or cell line. A "tumor sample" is a sample that includes at least one cell derived from at least one tumor.

The term "neoplasia", "cancer", "tumor", "cancerous", and "malignant" as used herein, refer to the physiological condition in mammals that is typically characterized by unregulated cell growth or the presence of tumors. Examples of cancer benefited by the present invention include, but are not limited to, adenocarcinoma, neuroendocrine carcinoma, squamous cell carcinoma, and urothelial carcinoma.

The term "classification" as used herein refers to a procedure or algorithm into which individual items are placed into groups or classes based upon quantitative information on one or more characteristics inherent in these items (referred to as traits, variables, characters, features, etc.) and based on a statistical model and/or a training set of previously labeled items.

The term "classifier" refers to a multivariate algebraic construct that is used to differentiate an individual item from another so that it can be placed into a specific class based on a training set. In the present application, the algebraic construct is used to obtain differentially expressed genes that may be used to classify carcinomas into one of four types: adenocarcinoma, neuroendocrine carcinoma, squamous cell carcinoma, and urothelial carcinoma. Subsequently an algebraic construct can be used to determine the primary site of tumor based on other differentially expressed genes.

"Top tier classifier(s)" as used herein refers to a single or group of classifier(s) that can be used to classify carcinomas into one of four types: adenocarcinoma, neuroendocrine carcinoma, squamous cell carcinoma, and urothelial carcinoma. Microarray expression data from the following 32 genes was used to train an artificial neural network with a single hidden node layer: HKDC1, KIAA0152, CALML4, ABP1, TRIM15, HNF4G, CRYL1, YAP1, KIF1A, ST18, SV2A, CRTAP, AIM1, TNFFRSF10B, LUZP1, S100A16, RPL39L, MGC35402, LAMP3, KRT5, ABCA13, PLEKHA6, LOC440552, DSC3, IFI16, ARHGAP23, GATA3, DHRS2, LRIG1, SEMA6D, LOC203274, and CERK. Top tier classifiers can include, but are not limited to, the above referenced differentially expressed genes as well as expression products of the genes and markers.

Figure 3:
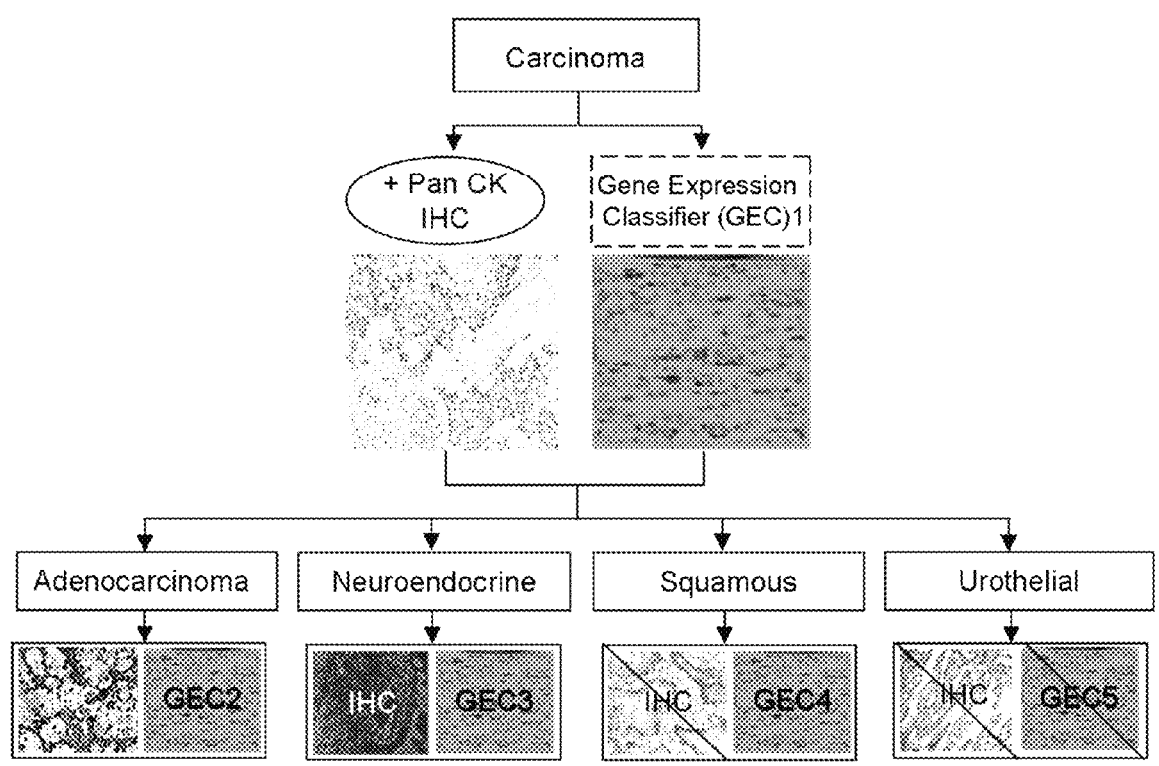
FIG. 3 is a flow diagram showing parallel and complementary gene expression classifier and IHC staining used to separate carcinoma into the four major subtypes. Strike thru line indicates no available IHC. No site of origin classifier was constructed for Urothelial as origin site plays no role in treatment decision.

"Second tier classifiers" refers to a group of four additional classifiers (as shown in FIG. 3) that are used to determine the site of origin for an unknown sample, and can be used subsequent to top tier classifiers to determine the primary site of origin for the tumor. The second tier classifiers may be organ-specific. The second tier classifiers for neuroendocrine carcinoma can include, but are not limited to: RHOC; ZFP36L2; CKAP1; LGALS4; NRD1; ADH7, ZNF24; PHF8; DES/// FAM48A; PRKCA; SCAMP2; CENTA1; C2orf26; FLJ22965; FLJ12355; ADM2; MYST3; CENTA1; EPS8L1; CRSP3; PBOV1; PCKH18; MSI2; ZNF71; CNKSR3; CCDC21; and AKAP13 as shown in FIG. 9. The second tier classifiers for squamous cell carcinoma include, but are not limited to: EIF5B; GJA1; CLCN3; PLS1; CUBN; HCN2; SFTPB; OGFR; CLASP2; CENTB2; OACT2; XTP2; SIX5; SNAP29; LPPR2; SFTPA2; METRN; RNF39; TAC3; RNASET2; DOCK6; C19orf22L; C1orf121; NAPSA; FBLIM1; STAT3; C8orf76; PLEKHG5; OACT1; PEBP4; FLJ10154; NDE1; FLJ10378L C20orf186; LOC221442; SHB; IGF1R; MSCP; HCMOGT-1; FAM76B; FLJ42289; EHMT1; WWOX; LOC162993; and RGS20 as shown in FIG. 10. The second tier classifiers for adenocarcinoma include, but are not limited to: MEST; PPP3CA; MEIS1; KLK3; TFAP2A; GAL3ST1; FXYD2; NDP; WT1; NOX1; FXYD2; D4S234E; GATA3; EYA2; SFTPB; CDH17; KLK2; IRX5; NAT8; MAB21L2; NOX1; TITF1; ATP2B4; FBXO21; LYPD1; KIAA0882; ATP2A3; SFTPB; PLEKHF2; MUC13; SOX17; OR51E2; SFTPB; MUC13; ELP3; PRLR; KLHL14; DPP6; SCGB3A2; LOC253970; CCDC4; SOX17; TITF1; DMGDH; LOC553137; PPP3CA; ACPP;

and TRPS1 as shown in FIG. 11. The specific probe sets used for the second tier classifiers are shown in FIGS. 9-11. Some genes are used in more than one probe set.

An "artificial neural network (ANN)" as used herein is a mathematical or computational model based on a biological neural network. In one embodiment, the ANN is an adaptive system that changes its structure based on external or internal information that flows through the network during a learning phase. The ANN in this case is an automated script that can be used to easily create a series of ANN architectures based on user supplied input parameters. In the ANN, a certain number of input nodes can be used to start and the number of input nodes can be sequentially increased by a predetermined number of input nodes until a given end number is reached.

The term "differential expression" as used herein refers to qualitative or quantitative differences in the temporal and/or spatial gene expression patterns within and among cells and tissues. A differentially expressed gene may qualitatively have its expression altered, including an activation or inactivation, such as in normal versus diseased tissue. Genes may be turned off or on in a given state relative to another state thus allowing comparison of two or more states. A qualitatively regulated gene may exhibit an expression pattern within a state or cell type that can be detectable by standard techniques. Alternatively, the difference in expression may be quantitative such that expression of the gene is modulated, up-regulated (resulting in an increased amount of transcript), or down-regulated (resulting in a decreased amount of transcript). The degree to which expression varies needs to be large enough to quantify via standard characterization techniques such as expression arrays, quantitative reverse transcriptase PCR, Northern blot analysis, real-time PCR, in situ hybridization, and RNase protection.

The term "expression profile" as used herein refers to a genomic expression profile, for example an expression profile of microRNAs. The profiles may be generated by any means for determining a level of a nucleic acid sequence, e.g. quantitative hybridization of microRNA, labeled microRNA, amplified microRNA, cDNA, quantitative PCR, ELISA for quantitation etc. The profile must allow for the analysis of differential gene expression between two samples. In some cases, the expression profile may refer to a gene product expression profile such as a protein expression profile.

The term "gene expression product" or "expression product" as used herein refers to an RNA transcribed from a gene (either pre- or post-processing) or an amino acid (e.g. a polypeptide, protein, or peptide regardless of any secondary modifications, such as glycosylation, lipidation or phosphorylation) encoded by the gene and generated by the gene when the gene is transcribed (either pre- or post-modification) and translated. An agent is said to increase gene expression if the application of a therapeutically effective amount of the agent to a cell or subject results in an increase in either an RNA or polypeptide expression product or both. An agent is said to decrease gene expression if the application of a therapeutically effective amount of the agent to a cell or subject results in a decrease in either an RNA or polypeptide expression product or both.

The term "polynucleotide" as used herein refers to a polymeric molecule that has a backbone that supports bases capable of hydrogen bonding to typical polynucleotides. The polymer backbone presents the bases in a manner that is effective to allow such hydrogen bonding in a sequence specific fashion between the polymeric molecule and a typical polynucleotide, such as single-stranded DNA. Polymeric molecules include both single and double stranded DNA or RNA and can include polymers having backbone modifications, it includes the recited sequences as well as their complementary sequences, which can be easily ascertained by those of ordinary skill in the art.

The term "polypeptide" as used herein refers to a compound made up of a single-chain of amino acid residues that are linked by peptide bonds. The term "protein" may be synonymous with the term "polypeptide" or may refer, in addition, to a complex of two or more polypeptides. Generally, polypeptides and proteins are formed predominantly of naturally occurring amino acids.

An "isolated polynucleotide" as used herein refers to a polynucleotide which is separated from other nucleic acid molecules which are present in the natural source of the polynucleotide. Preferably, an "isolated polynucleotide" is free of sequences which naturally flank the polynucleotide in the genomic DNA of the organism from which the nucleic acid is derived. An "isolated polynucleotide" is substantially free of other cellular material, gel materials, and culture medium when produced by recombinant techniques, or substantially free of chemical precursors or other chemicals when chemically synthesized. The polynucleotides of the present invention may be isolated from a variety of sources, such as PCR amplification from genomic DNA, mRNA, or cDNA libraries derived from the mRNA using standard techniques.

A "probe set" as used herein refers to a group of one or more polynucleotides that each selectively hybridize to the same target (for example, a specific genomic region or mRNA) that correlates with cancer diagnosis or prognosis. As such, a single "probe set" may comprise any number of different isolated polynucleotides that selectively hybridize to a given target. The probe sets used in the instant invention can be comprised of any number of probe sets from 1 probe set to 50 probe sets, including those numbers between 1 and 50. Some genes can be used in more than one probe set.

Standard pathological approaches combine morphology and immunohistochemical (IHC) studies to first subclassify cytokeratin positive carcinomas into adenocarcinoma, squamous cell carcinoma, neuroendocrine carcinoma and urothelial carcinoma. Subsequently, organ-specific IHC-markers, if available, are used to assign the primary site of origin to the sample. Microarray-based gene expression classifiers have shown promise in molecular classification of tumors, but have not been integrated into standard pathological algorithms and workflow and have been limited by sample sixes. Here a new hybrid approach was presented that combines IHC with a hierarchy of quantitative gene expression based classifiers into an algorithmic method that could assist pathologists to further refine and support their decision making process.

Assessment of morphological features using routine IHC stains is the first, and many times the last, step in pathological tumor classification, as many malignant neoplasms may be classified with morphology alone. Immunohistochemistry is often part of an algorithmic approach that first separates malignancies into general classes: hematolympboid, carcinomas, mesothelioma, melanoma, CNS primaries, germ cell neoplasms, and sarcomas. Specific subtypes within each category, except for melanoma and mesothelioma, may be further refined with the use of specific markers. The first key breakpoint is the distinction of hematolymphoid or liquid malignancies, from solid malignancies. The next breakpoint is distinguishing among the solid malignancies.

Figure 2:
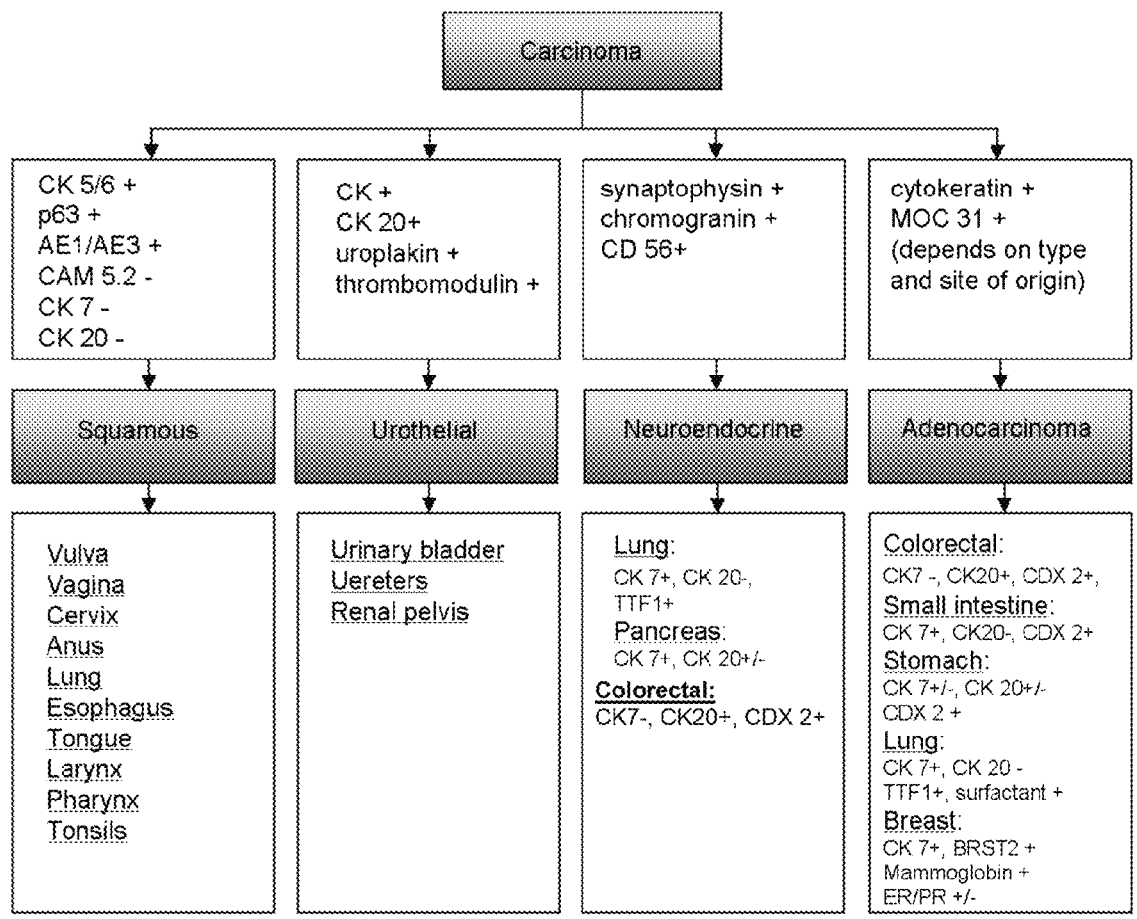
FIG. 2 is a flow diagram of immunohistochemical staining used to delineate four categories of carcinoma; when available, antibodies used in IHC are shown for primary site of origin identification. Note the absence of primary site of origin antibodies for Squamous and urothelial tissues.

Identification of cytokeratin expression is a key component of this algorithm, as it will delineate carcinomas, the most frequent type of adult malignancy. Mesothelioma and some germ cell tumors also express cytokeratins. Further immunohistochemical studies will separate mesothelioma and germ cell tumor from carcinomas (FIG. 1). Carcinomas are then further subtyped into squamous cell carcinoma, adenocarcinoma, neuroendocrine carcinoma and urothelial carcinoma; these may then be refined by site of origin (FIG. 2).

While the current antibody panels are relatively effective at distinguishing among these various forms of carcinoma, there remain instances in which the carcinoma type is not determined with objective certainty. Currently available antibody panels are used in a subjective and semi-quantitative manner by pathologists because of non-uniform criteria for determining what qualifies as positive expression.

The inability to distinguish carcinoma subtypes has therapeutic implications, because chemotherapeutic regimens for carcinomas are based not only on the site of primary origin but also on the subtype of carcinoma. As an example, the esophagus may develop both squamous cell carcinoma and adenocarcinoma, yet these different subtypes will receive a different type of chemotherapy. A neuroendocrine carcinoma will be treated with a specific type of therapy, depending on its differentiation, regardless of site of origin. Thus, a classification of human tumors which skips these distinctions would be missing significant information needed for appropriate treatment decisions.

In the present invention, a two tiered classification scheme was constructed based on gene expression data that first delineates neoplasms at the first branch point of cytokeratin positive malignancies, then delineates at the point of carcinoma differentiation, then determines a tumor's site of origin using a group of second tier classifiers (FIG. 3). FIGS. 9-11 list the genes that can be used as second tier classifiers for each of the three classification groups neuroendocrine carcinoma, adenocarcinoma, and squamous cell carcinoma. This classification process is performed in a quantitative and objective manner. Unlike other gene expression-based classification schemes proposed to date, this approach follows the standard work flow used in everyday practice of pathology and can be directly compared to or integrated with the results of IHC staining for each of these critical decision points (Bloom G, Yang I V, Boulware D, Kwong K Y, Coppola D, Eschrich S, Quackenbush J, Yeatman T J; Multi-platform, multi-site, microarray-based human tumor classification, Am J Pathol 2004, 164:9-16; Giordano, et al, Organ-specific molecular classification of primary lung, colon, and ovarian adenocarcinomas using gene expression profiles, Am J Pathol 2001, 159:1231-1238; Ramaswamy, et al., Multiclass cancer diagnosis using tumor gene expression signatures, Prod Natl Acad Sci USA 2991, 98:15149-15154; Su, et al., Molecular classification of human carcinomas by use of gene Expression signatures, Cancer Res 2001, 61:7388-7393).

The classification system described herein can be used to supplement or correlate to immunohistological data that is based on the algorithm currently used by pathologists. In an embodiment, instead of using immunohistochemistry, the two tiered classification system may be used on its own to identify primary point of origin for the neoplasm. The two-tiered classification system uses an artificial neural network (ANN) for classifier construction of top tier and second tier classifiers. The inventors used the following 32 genes as inputs for the ANN: HKDC1, KIAA0152, CALML4, ABP1, TRIM15, HNF4G, CRYL1, YAP1, KIF1A, ST18, SV2A, CRTAP, AIM1, TNFFRSF10B, LUZP1, S100A16, RPL39L, MGC35402, LAMP3, KRT5, ABCA13, PLEKHA6, LOC440552, DSC3, IFI16, ARHGAP23, GATA3, DHRS2, LRIG1, SEMA6D, LOC203274, and CERK. The top tier classifies can use gene microarray expression data to train the ANN. The second tier classifiers are subsequently inputted into the ANN. The use of the two-tiered classification system is capable of identifying the primary site of origin of the tumor.

The first step in the hybrid classification system described herein is to distinguish morphologically between solid and liquid tumor types. Cytokeratin immunohistochemistry (IHC) is then performed on the solid tumors to classify them as cytokeratin (+) or (−). Cytokeratin negative tumors consist of paraganglioma/pheochromocytoma, melanoma, lymphoma, leukemia, adrenal cortical carcinoma, and germ cell tumors. Immunochemistry using markers such as calretinin, WT1, PLAP and AFP is subsequently performed on the cytokeratin positive tumors to classify them as carcinoma, mesothelioma, or germ cell tumor. The carcinoma tumors are separated and immunochemistry as well as gene expression classifiers are used to classify the carcinomas into four subclassifications: adenocarcinoma, neuroendocrine carcinoma, squamous cell carcinoma, and urothelial carcinoma. Only adenocarcinoma, neuroendocrine carcinoma, and squamous cell carcinoma are used for the site of origin classifier since there is no available IHC for urothelial and origin site plays no role in treatment decision. The immunohistochemical markers used to classify the carcinomas into one of the four subclasses are shown in FIG. 2. IHC markers for squamous cell carcinoma include CK5/6+, p63+, AE1/AE3+, CAM5.2−, CK7−, and CK20−, IHC markers for urothelial carcinoma include, but are not limited to CK+, CK20+, uroplakin+, and thrombomodulin+. IHC markers for neuroendocrine carcinoma include, but are not limited to, synaptophysin+, chromogranin+, and CD56+. IHC markers for adenocacinoma include, but are not limited to, cytokeratin+ and MOC31+.

The gene expression classifiers are divided into top tier classifiers and second tier classifiers. Top tier classifier assigns a tumor to one of the four subclasses of carcinomas: adenocarcinoma, neuroendocrine carcinoma, squamous cell carcinoma, and urothelial carcinoma. Top tier classifiers include, but are not limited to, HKDC1, KIAA0152, CALML4, ABP1, TRIM15, HNF4G, CRYL1, YAP1, KIF1A, ST18, SV2A, CRTAP, AIM1, TNFFRSF10B, LUZP1, S100A16, RPL39L, MGC35402, LAMP3, KRT5, ABCA13, PLEKHA6, LOC440552, DSC3, IFI16, ARHGAP23, GATA3, DHRS2, LRIG1, SEMA6D, LOC203274, and CERK.

Three additional groups of second-tier classifiers assign the primary site of origin to the tumor within either adenocarcinoma, squamous cell carcinoma or neuroendocrine carcinoma classes dependent on initial classification. The second tier classifiers for neuroendocrine carcinoma can include, but are not limited to: RHOC; ZFP36L2; CKAP1; LGALS4; NRD1; ADH7, ZNF24; PHF8; DES///FAM48A; PRKCA; SCAMP2; CENTA1; C2orf26; FLJ22965; FLJ12355; ADM2; MYST3; CENTA1; EPS8L1; CRSP3; PBOV1; PCKH18; MSI2; ZNF71; CNKSR3; CCDC21; and AKAP13 as shown in FIG. 9. The second tier classifiers for squamous cell carcinoma include, but are not limited to: EIF5B; GJA1; CLCN3; PLS1; CUBN; HCN2; SFTPB; OGFR; CLASP2; CENTB2; OACT2; XTP2; SIX5; SNAP29; LPPR2; SFTPA2; METRN; RNF39; TAC3; RNASET2; DOCK6; C19orf22L; C1orf121; NAPSA; FBLIM1; STAT3; C8orf76; PLEKHG5; OACT1; PEBP4; FLJ10154; NDE1; FLJ10378L C10orf186; LOC221442; SHB; IGF1R; MSCP; HCMOGT-1; FAM76B; FLJ42289; EHMT1; WWOX; LOC162993; and RGS20 as shown in FIG. 10. The second tier classifiers for adenocarcinoma include, but are not limited to: MEST; PPP3CA; MEIS1; KLK3; TFAP2A; GAL3ST1; FXYD2; NDP; WT1; NOX1; FXYD2; D4S234E; GATA3; EYA2; SFTPB; CDH17; KLK2; IRX5; NAT8; MAB21L2; NOX1;

TITF1; ATP2B4; FBXO21; LYPD1; KIAA0882; ATP2A3; SFTPB; PLEKHF2; MUC13; SOX17; OR51E2; SFTPB; MUC13; ELP3; PRLR; KLHL14; DPP6; SCGB3A2; LOC253970; CCDC4; SOX17; TITF1; DMGDH; LOC553137; PPP3CA; ACPP; and TRPS1 as shown in FIG. 11. The specific probe sets used for the second tier classifiers are shown in FIGS. 9-11. The second tier classifiers can be organ-specific. In use, the IHC data can be used in conjunction with the gene expression classifiers to determine carcinoma type as well as tissue of origin.

A set of 561 samples were selected from a pool of over 2300 carcinomas arrayed on the same whole genome microarray platform for use in this study. Classifiers were constructed by an initial one vs. all feature selection approach to obtain genes most correlated with differentiation of the four types of carcinomas. The resultant gene set was used to train an artificial neural network. All classifiers were evaluated by both leave-one-out cross validation and an independent testing set.

First tier classifier accuracies were 89%, 88% and 75% for the cross-validation, independent, and institutional independent test sets respectively. Second tier classifier accuracies were 87%, 90% and 87% for adenocarcinoma, squamous and neuroendocrine carcinoma respectively, thereby demonstrating successful separation of the four main subtypes of carcinoma and subsequent assignment of primary site of origin by incorporation of gene expression based classifiers into the standard algorithmic pathology approach.

Sources of Human Microarray Data

Data used to build all classifiers were exclusively derived from tissues arrayed on Affymetrix U133 Plus 2.0 Gene Chips (Asymetrix, Santa Clara, Calif.). Two sets of data were utilized: microarray data published by the International Genomics Consortium Expression Project for Oncology (expO) and data derived from fresh frozen samples obtained from Moffitt Cancer Center tumor bank.

IGC expO has published over 1900 tumor samples that have been analyzed on the identical U133 Plus 2.0 Gene Chips, making the derived data comparable. The pathology information accompanying each sample was reviewed by a single pathologist (B.A.C.) to delineate the epithelial malignancies into one of the four carcinoma subtypes and into a primary site of origin. Only primary tumors were considered for the analysis. A total set of 561 carcinoma samples were used in the study.

FIG. 4 lists all carcinoma types obtained from the expO dataset. Heparocellular carcinomas and renal cell carcinomas were delineated as adenocarcinomas for the purpose of this study. In this cohort, adenocarcinomas represent the greatest number of carcinoma subtypes, followed by squamous cell carcinomas, urothelial carcinomas and neuroendocrine carcinomas.

In addition to the expO data set, 413 tumor samples obtained from the Moffitt Cancer Center tumor bank were arrayed using the U133 Plus 2.0 GeneChip from Affymetrix. A summary of the tumor types and primary sites of origin profiled are listed in FIG. 5. As for the expO data, all tumor samples derived from the Moffitt Cancer Center tumor bank were reviewed by a single pathologist (B.A.C.). Cases were selected to include morphological variants when applicable, and to include all grades of differentiation to develop classifiers that will be applicable to the widest range of histologic variants of these malignancies. RNA Extraction was performed using the RNeasy Mini Kit by Qiagen (Valencia, Calif.). RNase activity was minimalized by using the RNase-free DNase Set by Qiagen. Standard protocols for each of these products were followed. Specimen quality was assessed using Agilent BioAnalyzer (Agilent, Santa Clara, Calif.). The Bio-analyzer software calculates an RNA integrity number on a scale from 1 to 10 for each RNA sample run on the chip. An RNA integrity number >6.5 was taken as the cut-off for accepting the RNA as being of good quality. Specimens that were not of good quality were discarded.

Expression Value Calculation (RMA)

Robust Multi-Array Analysis (RMA) was used to normalize calculate gene expression values for all samples used. Each sample was treated independently for the purposes of classifier training and testing to ensure that there was no unwanted bias.

Expression Value Calculation (Incremental RMA)

Incremental RMA (iRMA) is a technique wherein the quantile normalization means and probe binding affinity parameters from one sample set are saved during the RMA procedure. These two value sets are then used directly by subsequent RMA procedures in lieu of recalculation of these model values for the new sample set (Eschrich, et al., Tissue-specific RMA models to incrementally normalize Affymetrix GeneChip data, Conf Proc IEEE Eng Med Biol Soc 2008, 1:2419-2422). This approach allows for the normalization of gene expression data from different sources to an initial data set without the need to perform RMA on the entire sample set due to the addition of a new sample or set of samples. In the same manner iRMA can be used to normalize an independent test set to the training set on which a classifier was built allowing independent testing of data without the introduction of chip set bias. Expression values for all Independent Test sets were calculated with iRMA using the quantile means and probe binding affinities derived from the previous RMA procedure on the corresponding Training-Test split set.

Construction of the Carcinoma Subtype Classifier

Training—Test Split

The initial training set consisted of 30 randomly selected samples each of squamous cell carcinoma, adenocarcinoma, and urothelial carcinoma and 11 cases of neuroendocrine carcinoma, obtained from the expO data set. All available cases of neuroendocrine carcinoma were used (n=11).

Independent Test Set

The initial independent test set consisted of an additional randomly selected 10 samples of squamous cell carcinoma, adenocarcinoma, and urothelial carcinoma. No additional neuroendocrine samples were available from expO. All samples were obtained from the expO dataset. Samples used in the Training Test split were not considered for selection here, as is the case for all independent test sets described.

Institutional Independent Test Set

The institutional independent test set consisted of randomly selected tissues from the Moffitt Cancer Center data set (n=413 tumor samples). Twenty samples each of squamous cell carcinoma, adenocarcinoma, urothelial carcinoma, and neuroendocrine carcinoma were used for testing.

Construction of Adenocarcinoma Primary Site Classifier

Training—Test Split

The initial training set consisted of 20 randomly selected samples each of kidney, ovary, uterus, colon, lung, prostate, breast (n=140) obtained from the combined expO dataset and Moffitt derived data. RMA was used for normalization and gene expression signal calculation.

Independent Test Set

The independent test set consisted of 10 randomly selected samples each of kidney, ovary, uterus, colon, lung, prostate, and breast obtained from the combined expO and Moffitt data sets. Incremental RMA was applied to this data set using the model values obtained during RMA of the initial training set.

Construction of Squamous Primary Site Classifier

Training—Test Split

The initial training set consisted of 25 randomly selected samples from a combined tongue and larynx group. Additionally, 3 vulva, 9 cervix, 5 penis, 18 lung and 8 rectum were randomly selected from the combined expO and Moffitt data set RMA was used for gene expression signal calculation.

Independent Test Set

The independent test set consisted of 11 randomly selected samples from a combined, tongue and larynx group. Additionally, 2 vulvar, 4 cervical, 2 penile, 6 pulmonary and 4 rectal squamous cell carcinomas were randomly selected from the combined expO and Moffitt data set. Incremental RMA was applied to this data set using the model values obtained during RMA of the initial training set.

Construction or Neuroendocrine Primary Site Classifier

Training—Test Split

The initial training set consisted of 11 randomly selected samples from a combined small bowel and duodenum group. Additionally 7 pancreatic and 11 lung neuroendocrine carcinomas were randomly selected from the combined expO and Moffitt data set RMA was used for gene expression signal calculation.

Independent Test Set

The independent set consisted of 6 randomly selected samples from a combined small bowel and duodenum group. Additionally, 4 pancreatic and 4 lung neuroendocrine neoplasms were randomly selected from the combined expO and Moffitt data set. Incremental RMA was applied to this data set using the model values obtained during RMA of the initial training set.

Identification of Discriminating Genes—Feature Selection

Identification of a relatively small number of genes that have the ability to distinguish between different tumor categories is a great challenge that is inherent in all large-scale biological assays. To avoid the possibility of selecting a list of genes for the classifier where many or all of the highly significant genes distinguish a minimal number of tumor categories, the following approach was used.

A series of 4 Kruskal-Wallis H tests were performed comparing a single tumor category versus the 3 remaining tumor categories. This "one vs. all" approach results in 4 lists of probe sets that were subsequently sorted by p-value. To construct a classifier with n=50 probe sets, the top probe sets were chosen from each of the 4 lists and then continued to the second probe set from each list. This process was repeated until n=50 probe sets were chosen. Note that since a single gene is represented by more than one probe set on the Affymetrix U133 Plus chip, the list consists of 50 probe sets rather than 50 individual genes.

Classifier Construction

An artificial neural network (ANN) was chosen for the classifier construction due to its Ability to approximate any nonlinear function reasonably well and because no a priori assumptions need to be made about the relative importance of any single feature. Fifty input features (probe sets) and five hidden nodes were used to train the ANN for all classifiers constructed. A leave-k-out cross validation (LKOCV), k=10%, was used to assess the accuracy of all constructed classifiers. LKOCV in some cases can be slightly optimistic, and two independent training sets were used for further validation in the case of the carcinoma subtype classifier. It should be noted that a "complete" analysis was performed for each sample, meaning that both the gene selection procedure and subsequent ANN training steps were performed for each fold.

Classifier Accuracies

The accuracies for the cross validation of the training set and each of the test sets is shown as confusion matrix tables (FIG. 6) for the carcinoma subtype classifier. The confusion matrix tables show class by class accuracy and cumulative accuracy. The first independent test set did not include neuroendocrine carcinomas. The training set established an accuracy of 89%. The accuracy of the first independent test set was 88%. An institutional independent test set, in which all samples originated from the Moffitt tissue bank, resulted in 78% accuracy in separation Of the four carcinoma subtypes.

The underlying primary site of origin for the IGC tumors, training set, was notably different from the Moffitt tumors, institutional training set contributing to the drop in accuracy. Accuracies for each of the three sites of origin classifiers are presented in FIG. 7. Confusion matrices and accuracies for the training cross-validation and independent test sets are presented.

Gene Function Analysis

A total of 32 discriminating genes were identified from the list of 50 Affymetrix probe sets, shown in FIG. 7. Most of the genes identified are not well characterized or studied in human tumors. However, the protein expression of four of these genes has been previously validated in human tissues. One such example is synaptic vesicle glycoprotein 2A (SV2A), a gene identified as a marker of neuroendocrine carcinomas. SV2 is an integral membrane protein, similar to synaptophysin, a well established marker of neuroendocrine differentiation. SV2A is one of three well characterized isoforms of SV2 which include SV2A, SV2B and SV2C. SV2 immunoreactivity has been observed in neuroendocrine cells of normal stomach, intestines, parathyroid, thyroid, pancreas, and adrenal medulla, as well as nerve structures in all organs (Portela-Gomes, et al., Synaptic vesicle protein 2, A new neuroendocrine cell marker. Am J Pathol 2000, 157:1299-13). SV2 was found to be expressed in neuroendocrine carcinomas from a variety of organs (Portela-Gomes, et al., Synaptic vesicle protein 2, A new neuroendocrine cell marker, Am J Pathol 2000, 157:1299-1309; Jakobsen, et al., Expression of synaptic vesicle protein 2 (SV2) in neuroendocrine tumors of the gastrointestinal tract and pancreas, J Pathol 2002, 196:44-50).

Cytokeratin 5, found as a marker of squamous cell carcinoma, is an established component of the antibody panel used to distinguish squamous cell carcinomas from the other carcinoma types. The antibody to cytokeratin 5/6 combined with p63 is routinely used by pathologists to distinguish squamous cell carcinoma from adenocarcinoma and neuroendocrine carcinomas and a number of publications have confirmed its utility for specific problematic morphological differential diagnoses (Kaufmann, et al., Value of p63 and cytokeratin 5/6 as undifferentiated carcinomas, Am J Clin Pathol 2001, 116: 823-830; Kargi, et al., The diagnostic value of TTF-1, CK 5/6, and p63 immunostaining in classification of lung carcinomas, Appl Immunohistochem Mol Morphol 2007, 15:415-420; Serrano, et al., Utility of high molecular weight cytokeratins, but not p63, in the differential diagnosis of neuroendocrine and basaloid carcinomas of the head and neck, Hum Pathol 2008, 39:591-509; Khayyata, et al., Value of P63 and CK5/6 in distinguishing squamous cell carcinoma from adenocarcinoma in lung fine-needle aspiration specimens, Diagn Cytopathol 2009, 37:178-183). Diffuse expression for CK5/6 is a marker of squamous differentiation (Chu and Weiss, Expression of cytokeratin 5/6 in epithelial neoplasms: an immunohistochemical study of 509 cases, Mod Pathol 2002, 15:6-10).

Desmcollin-3 was shown, to have differential expression between squamous cell carcinoma and the other carcinoma subtypes. Immunohistochemical analysis of lung carcinomas showed desmocollin-3 to be expressed in all squamous cell carcinomas, but in only 2 to 19 adenocarcinomas and 50% of large cell carcinomas. This study validates these findings (Monica, et al., Desmocollin-3: a new marker of squamous differentiation in undifferentiated large-cell carcinoma of the lung, Mol Pathol 2009, 22:709-717).

HNF4 is a marker of adenocarcinoma. One study found HNF4 alpha to be a marker of ovarian mucinous carcinomas in fluids (Sugai et al., Expression of hepatocyte nuclear factor 4 alpha in primary ovarian mucinous tumors, Pathol Int 2008, 58:681-686). The exact specificity of HNF4 gamma remains to be studied. HNF4 gamma is expressed in the kidneys, gut, pancreas and testes. (Gerdin A. K. et al., Phenotypic screening of hepatocyte nuclear factor (HNF) 4-gamma receptor knockout mice. Biochem Biophys Res Commun. 2006, 349: 825-832)

A new hybrid approach that combines morphological, and IHC assessment with a hierarchy of quantitative gene expression-based classifiers into the algorithmic method currently used by pathologists was successfully developed and tested. This approach incorporates a hierarchy of gene expression-based classifiers into the algorithmic method currently used by the pathologist to further refine and support their decision making process.

The algorithm was initiated at the point where the pathologist typically engages: differentiating a neoplasm as carcinoma based on morphology and immunophenotypic expression for cytokeratins, and then determining whether it falls into one of four main subtypes of carcinoma. The first tier of the molecular classifier of the present invention similarly begins by assigning a neoplasm defined as carcinoma (based on morphology and cytokeratin expression) into one of four carcinoma subtypes: squamous cell, neuroendocrine, adenocarcinoma, and urothelial. First tier classifier accuracies were 89%, 88% and 75% for cross-validation, independent, and institutional independent test sets, respectively, showing an ability to separate these four subtypes of carcinoma. The identification of SV2, desmocollin-3, CK5 and HNF4 as discriminating genes effectively validates this first tier of the classifier since these proteins have already been demonstrated to be useful in differential diagnosis. This selection of genes for the first tier classifier is based on real biological differences since these proteins have already been shown to be differentially expressed in these human tissues. While many carcinomas are easy subclassify, some pose a challenge because they are poorly differentiated or appear to show combined features of differentiation, such as combined neuroendocrine carcinoma and adenocarcinoma or squamous cell carcinoma or combined adeno- and squamous cell carcinoma.

The next step in pathological assessment is to subclassify the carcinoma relative to the site of primary origin. Current immunohistochemical algorithms to define site of origin are only applicable to adenocarcinomas and well-differentiated neuroendocrine carcinomas. Although the antibody panels are effective at generally narrowing down possible primary sites, they are used in a subjective and qualitative or semi-quantitative manner. Furthermore, squamous cell carcinomas are not classifiable by site of primary origin utilizing currently available antibody panels.

Standard pathology work flow was followed, as described above, by developing a second tier of classifiers that assigned the primary site of origin to the tumor within adenocarcinoma, squamous cell carcinoma or neuroendocrine carcinoma dependent on initial classification. Second tier classifier accuracies ranged from 83% to 93%, showing the ability of the gene expression-based classifiers to distinguish a large variety of primary sites.

A number of studies have demonstrated accurate prediction of tumor class by using gene expression-based tumor classification schemes. Most of these gene expression based classifiers have started with an all-encompassing approach that did not incorporate differences in tumor cell morphology and biology. These studies included solid and liquid tumor types, and unrelated tumor types such as melanoma, carcinoma and CNS malignancies, all of which are usually easily distinguished with histomorphology and IHC, thus not requiring or benefiting from a molecular classification strategy. (Bloom, et al., Multi-platform, multi-site, microarray-based human tumor classification, Am J Pathol 2004, 164:9-16; Ma, et al., Molecular classification of human cancers using 92-gene real-time quantitative polymerase chain reaction assay, Arch Pathol Lab Med 2006, 130:465-473; Ramaswamy, et al., Multiclass cancer diagnosis using tumor gene expression signatures, Proc Natl Acad Sci USA 2001, 98:15149-15154) Additionally, other studies have focused solely on subclassifying a limited spectrum of Carcinomas as to site of origin, without distinction as to carcinoma subtype. (Buckhaults, et al., Identifying tumor origin using a gene expression-based classification map, Cancer Res 2003, 63:4144-4149; Giordano, et al., Organ-specific molecular classification of primary lung, colon, and ovarian adenocarcinomas using gene expression profiles, Am J Pathol 2001, 159:1231-1238; Su, et al., Molecular classification of human carcinomas by use of gene expression signatures, Cancer Res 2001, 61:7388-7393; Tothill, et al., An expression-based site of origin diagnostic method designed for clinical application to cancer of unknown origin, Cancer Res 2005, 65:4031-4040) None of these studies incorporated an approach following an algorithm familiar to the pathologist.

Adenocarcinomas are known to have significant morphological variation; therefore, subtype is as important as the site of primary origin. Carcinoma subtype impacts the tumor classification. As an example, mucinous ovarian carcinomas classify with colonic or gastrointestinal primaries rather than with ovarian serous type carcinomas. (Giordano, et al., Organ-specific molecular classification of primary lung, colon, and ovarian adenocarcinomas using gene expressing profiles, Am J Pathol 2001, 159:1231-1238, Tothill, et al., An expression-based site of origin diagnostic method designed for clinical application to cancer of unknown origin, Cancer Res 2005, 65:4031-4040) This demonstrates the necessity of including a variety of tumor subtypes and grades associated with a particular tumor class. For this reason, the classifier of the present invention is built on a variety of adenocarcinoma types per organ site and includes the various grades of differentiation per type.

The classification system of the present invention is the first to show successful classification of two other subtypes of carcinoma: squamous cell and neuroendocrine carcinoma. The squamous cell carcinoma classifier included vulva, cervix, penile, pulmonary and ano-rectal carcinomas. In clinical practice, vulvar, cervical and penile carcinomas would not be considered in the same patient, as these are gender specific cancers. However, this classifier serves as a proof of principle for using gene-expression based classification for squamous cell carcinomas. Interestingly, the tongue and larynx primaries could not be separated, indicating the close embryological relationship of these organs. The classifier may be expanded by adding additional possible primary sites from the head, neck, and esophagus.

Neuroendocrine carcinoma, unknown primary continues to be a diagnostic problem in the current practice of oncology and pathology. Frequent sites of metastases include liver, lymph nodes and bone. In a recent analysis of SEER data, up to 21% of low grade and 50% of high-grade neuroendocrine carcinomas were associated with metastases at the time of diagnosis (Yao, et al., One hundred years after "carcinoid", epidemiology of and prognostic factors for neuroendocrine tumors in 35,825 cases in the United States, J Clin Oncol 2008, 26:3063-3072). In a proportion of these malignancies, the site of primary neuroendocrine carcinoma is not clinically evident. It is, therefore, important to develop diagnostic tools to accurately predict the origin of metastatic neuroendocrine carcinoma, so that the primary tumor may also be treated appropriately. The neuroendocrine carcinomas included in this analysis were front the three most frequent primary sites, pancreas, small bowel and lung. Missing from these primaries is Merkel cell carcinoma, a primary high-grade neuroendocrine carcinoma of the skin. Merkel cell carcinoma may be distinguished from other neuroendocrine carcinomas by its characteristic CK 7-negative and CK 20-positive immunophenotypic pattern. IHC markers that can be used to determine the site of origin of 'metastatic low-grade neuroendocrine carcinomas' from unknown primary sites include TTF1, CDX2, cytokeratin 7 and 20, neuroendocrine secretory protein-55 NESP55) and pancreatic and duodenal homeobox factor-1 (PDX-1) (Cai, et al., Cytokeratin 7 and 20 and thyroid transcription factor 1 can help distinguish pulmonary from gastrointestinal carcinoid and pancreatic endocrine tumors, Hum Pathol 2001, 32:1087-1093; Jakobsen, et al., NESP55, a novel chromogranin-like peptide, is expressed in endocrine tumors of the pancreas and adrenal medulla but not in ileal carcinoids. Br J Cancer 2003, 88:746-1754; Srivastava, et al., Neuroendocrine secretory protein-55 (NESP-55) expression discriminates pancreatic endocrine tumors and pheochromocytomas from gastrointestinal and pulmonary carcinoids, Am J Surg Pathol 2004, 28:1371-1378; Srivastava and Hornick, Immunohistochemical staining for CDX-2, PDX-1, NESP-55, and TTF-1 can help distinguish gastrointestinal carcinoid tumors from pancreatic endocrine and pulmonary carcinoid tumors, Am J Surg Pathol 2009, 33:626-632). Despite site-specificity of these markers, a number of metastatic low-grade neuroendocrine carcinomas in the liver and other metastatic sites remain in the 'unknown primary' category. The molecular classifier proposed herein is a useful adjunct to the currently available IHC markers for more accurate prediction of primary site of origin in case of metastatic neuroendocrine carcinomas from unknown primary sites.

In summary, standard pathological approaches combine morphology and immunohistochemical (IHC) studies to first subclassify cytokeratin-positive carcinomas into adenocarcinoma, squamous cell carcinoma, neuroendocrine carcinoma, and urothelial carcinoma. Subsequently, organ-specific IHC-markers are used to assign the tumor's primary site of origin. The novel hybrid approach presented herein integrates a hierarchy of gene expression classifiers into the algorithmic method used with IHC. The method presented herein first assigns the tumor to one of the carcinoma subclasses by the top tier classifier. Dependent on initial classification, one of three second tier classifiers assigns a primary site which results in both carcinoma subtype and primary site classification.

Distinction among the four basic subtypes of carcinoma and subsequent delineation of primary site of origin is feasible using a tumor classifier derived from standard practice based on morphology and immunohistochemistry, integrated with microarray-based gene expression profiling. This hybrid approach follows the standard pathological workflow for carcinoma classification. This success allows for both integration and direct comparison of microarray based classifiers to established pathological techniques for distinguishing carcinomas of unknown primary.

In the preceding specification, all documents, acts, or information disclosed does not constitute an admission that the document, act, or information of any combination thereof was publicly available, known, to the public, part of the general knowledge in the art, or was known to be relevant to solve any problem at the time of priority.

The disclosures of all publications cited above are expressly incorporated herein by reference, each in it entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between. Now that the invention has been described.

What is claimed is:

1. A method of identifying the origin of a neoplasm of unknown primary comprising:

obtaining a sample of a neoplasm;

analyzing morphology of the sample to distinguish between solid and liquid tumor types;

testing the solid sample for cytokeratin expression to determine if the solid sample is cytokeratin positive or negative;

performing immunohistochemistry on the cytokeratin positive sample to differentiate between carcinoma, mesothelioma and germ cell tumors;

performing immunohistochemistry on the carcinoma sample to differentiate between subclasses of carcinomas wherein the subclasses of carcinoma are selected from the group consisting of adenocarcinoma, squamous cell carcinoma, urothelial carcinoma, and neuroendocrine carcinoma;

applying a hierarchal microarray gene expression classifier to gene expression data from the carcinoma sample to verify differentiation between the subclasses of the carcinomas wherein the hierarchal gene expression classifier is comprised of top tier classifiers and second tier classifiers;

assigning the carcinoma sample to one of the subclasses of carcinoma based on comparing the immunohistochemistry and the top tier classifier results;

applying the second tier classifier to gene expression data from the carcinoma sample to assign a primary site of origin to the carcinoma sample; and administering a treatment to the patient according to the subclass of carcinoma assigned to the carcinoma sample;

wherein the top tier classifiers differentiate between the subclasses of the carcinomas wherein the subclasses of carcinoma are selected from the group consisting of adenocarcinoma, squamous cell carcinoma, urothelial carcinoma, and neuroendocrine carcinoma;

wherein the top tier classifiers for adenocarcinoma use gene expression data selected from the group of genes consisting of hexokinase domain containing 1 (HKDC1), malectin (KIAA0152), calmodulin-like 4 (CALML4), amiloride binding protein 1 (ABP1), tripartite motif-containing 15 (TRIM15), hepatocyte nuclear factor 4 gamma (HNF4G), and crystallin lambda 1 (CRYL1).

2. The method of claim 1, wherein the top tier classifier for adenocarcinoma uses gene expression data from HNF4.

3. The method of claim 1, wherein the top tier classifiers for neuroendocrine carcinoma use gene expression data selected from the group of genes consisting of YAP1, KIF1A, ST18, SV2A, CRTAP, AIM1, TNFFRSF10B, LUZP1, and S100A16.

4. The method of claim 1, wherein the top tier classifier for neuroendocrine carcinoma uses gene expression data from SV2A.

5. The method of claim 1, wherein the top tier classifiers for squamous cell carcinoma use gene expression data selected from the group of genes consisting of RPL39L, MGC35402, LAMP3, KRT5, ABCA13, PLEKHA6, LOC440552, DSC3, and IFI16.

6. The method of claim 1, wherein the top tier classifier for squamous cell carcinoma uses gene expression data from cytokeratin 5.

7. The method of claim 1, wherein the top tier classifier for squamous cell carcinoma uses gene expression data from desmocollin-3.

8. The method of claim 1, wherein the top tier classifiers for urothelial carcinoma use gene expression data selected from the group of genes consisting of ARHGAP23, GATA3, DHRS2, LRIG1, SEMA6D, LOC203274, and CERK.

9. The method of claim 1, wherein the second tier classifiers are assigned to one of three subclasses of carcinomas selected from the group consisting of squamous cell carcinoma, neuroendocrine carcinoma, and adenocarcinoma to determine a primary site of origin of the tumor.

10. A method of identifying the origin of a neoplasm of unknown primary comprising:
  obtaining a sample of a neoplasm;
  obtaining morphological data of the neoplasm sample to distinguish between solid and liquid tumor types;
  testing the solid sample for cytokeratin expression to determine if the solid sample is cytokeratin positive or negative;
  performing immunohistochemistry on the cytokeratin positive sample to differentiate between carcinoma, mesothelioma and germ cell tumors;
  obtaining microarray-based gene expression data for the carcinoma sample;
  applying a hierarchal microarray gene expression classifier to the gene expression data for the carcinoma sample to differentiate between subclasses of carcinomas wherein the hierarchal gene expression classifier is comprised of top tier classifiers and second tier classifiers wherein the top tier classifiers differentiate between the subclasses of carcinomas wherein the subclasses of carcinoma are selected from the group consisting of adenocarcinoma, squamous cell carcinoma, urothelial carcinoma, and neuroendocrine carcinoma;
  assigning the carcinoma sample to one of the subclasses of carcinoma based on the top tier classifiers;
  assigning the carcinoma sample to a primary site of origin based on the second tier classifiers; and
  administering treatment to the patient according to the determined primary site of origin of the carcinoma sample;
  wherein the top tier classifiers for adenocarcinoma use gene expression data selected from the group of genes consisting of hexokinase domain containing 1 (HKDC1), malectin (KIAA0152), calmodulin-like 4 (CALML4), amiloride binding protein 1 (ABP1), tripartite motif-containing 15 (TRIM15), hepatocyte nuclear factor 4 gamma (HNF4G), and crystallin lambda 1 (CRYL1).

11. The method of claim 10, further comprising:
  performing immunohistochemistry on the carcinoma sample to assign the carcinoma sample to one of the subclasses of carcinomas; and
  comparing the immunohistochemistry data from the carcinoma to the microarray-based gene expression data to verify the subclass prior to applying the second tier classifiers.

12. The method of claim 10, wherein the top tier classifiers for neuroendocrine carcinoma use gene expression data selected from the group of genes consisting of YAP1, KIF1A, ST18, SV2A, CRTAP, AIM1, TNFFRSF10B, LUZP1, and S100A16.

13. The method of claim 10, wherein the top tier classifiers for squamous cell carcinoma use gene expression data selected from the group of genes consisting of RPL39L, MGC35402, LAMP3, KRT5, ABCA13, PLEKHA6, LOC440552, DSC3, and IFI16.

14. The method of claim 10, wherein the top tier classifiers for urothelial carcinoma use gene expression data selected from the group of genes consisting of ARHGAP23, GATA3, DHRS2, LRIG1, SEMA6D, LOC203274, and CERK.

15. The method of claim 10, wherein the second tier classifiers are assigned to one of three subclasses of carcinomas selected from the group consisting of squamous cell carcinoma, neuroendocrine carcinoma, and adenocarcinoma to determine a primary site of origin of the tumor.

16. A method of identifying the origin of a neoplasm of unknown primary comprising:
  obtaining a sample of a neoplasm;
  obtaining morphological data of the neoplasm sample to distinguish between solid and liquid tumor types;
  performing immunohistochemistry on the solid sample for cytokeratin expression to determine if the solid sample is cytokeratin positive or negative;
  differentiating the cytokeratin positive neoplasm sample between carcinoma, mesothelioma and germ cell tumors using immunohistochemistry;
  obtaining microarray-based gene expression data for the carcinoma sample;
  training an artificial neural network (ANN) to develop a hierarchal microarray gene expression classifier comprised of top tier classifiers and second tier classifiers;
  differentiating the carcinoma sample between one of four subclasses of carcinomas selected from the group consisting of squamous cell carcinoma, urothelial carcinoma, neuroendocrine carcinoma, and adenocarcinoma using the top tier classifiers;
  utilizing the second tier classifiers to classify the carcinoma sample according to primary site of origin; and
  administering treatment to the patient according to the determined primary site of origin of the carcinoma sample;
  wherein the top tier classifiers for adenocarcinoma use gene expression data selected from the group of genes consisting of HKDC1, KIAA0152, CALML4, ABP1, TRIM15, HNF4G, and CRYL1.

17. The method of claim 16, further comprising performing immunohistochemistry on the cytokeratin positive carcinoma sample to assign the carcinoma sample to one of the subclasses of carcinomas; and comparing the immunohistochemistry data from the carcinomas to the microarray-based gene expression data to verify the subclass prior to applying the second tier classifiers.

18. The method of claim 17, wherein the top tier classifiers for neuroendocrine carcinoma use gene expression data selected from the group of genes consisting of YAP1, KIF1A, ST18, SV2A, CRTAP, AIM1, TNFFRSF10B, LUZP1, and S100A16.

19. The method of claim 17, wherein the top tier classifiers for squamous cell carcinoma use gene expression data selected from the group of genes consisting of RPL39L, MGC35402, LAMP3, KRT5, ABCA13, PLEKHA6, LOC440552, DSC3, and IFI116.

20. The method of claim 17, wherein the top tier classifiers for urothelial carcinoma use gene expression data selected from the group of genes consisting of ARHGAP23, GATA3, DHRS2, LRIG1, SEMA6D, LOC203274 and CERK.

21. The method of claim 16, wherein the second tier classifiers are assigned to one of three subclasses of carcinomas selected from the group consisting of squamous cell carcinoma, neuroendocrine carcinoma, and adenocarcinoma to determine a primary site of origin of the tumor.

\* \* \* \* \*